(12) United States Patent
Kagawa

(10) Patent No.: US 10,575,720 B2
(45) Date of Patent: Mar. 3, 2020

(54) ENDOSCOPE SYSTEM

(71) Applicant: OLYMPUS CORPORATION, Tokyo (JP)

(72) Inventor: Ryohei Kagawa, Hachioji-shi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/590,461

(22) Filed: May 9, 2017

(65) Prior Publication Data

US 2017/0238791 A1     Aug. 24, 2017

Related U.S. Application Data

(63) Continuation of application No. PCT/JP2016/050506, filed on Jan. 8, 2016.

(30) Foreign Application Priority Data

Jan. 16, 2015   (JP) .................................. 2015-007078

(51) Int. Cl.
*A61B 1/00*      (2006.01)
*A61B 1/06*      (2006.01)

(52) U.S. Cl.
CPC ........ *A61B 1/0638* (2013.01); *A61B 1/00009* (2013.01); *A61B 1/00057* (2013.01)

(58) Field of Classification Search
CPC ............ G02B 23/2469; G02B 23/2461; G02B 23/2484; G02B 23/26; G02B 23/24;
(Continued)

(56) References Cited

U.S. PATENT DOCUMENTS

| 8,785,833 B2 | 7/2014 | Yabe et al. |
| 2014/0364690 A1 | 12/2014 | Seto |
| 2016/0120398 A1* | 5/2016 | Kubo ................... A61B 1/0638 348/68 |

FOREIGN PATENT DOCUMENTS

| JP | 2013-202189 A | 10/2013 |
| JP | 2014-183908 A | 10/2014 |

(Continued)

OTHER PUBLICATIONS

International Search Report dated Apr. 5, 2016 issued in PCT/JP2016/050506.

(Continued)

*Primary Examiner* — Alexandra L Newton
(74) *Attorney, Agent, or Firm* — Scully, Scott, Murphy & Presser, P.C.

(57) ABSTRACT

An endoscope system includes: a light source device for sequentially emitting illumination light of three colors; an image sensor having pixels to perform photoelectric conversion on light from an object irradiated with the illumination light and output image signals; an illumination controller for causing the light source device to emit the illumination light of two colors during a one-line exposure period of the image sensor; and a calculation unit for calculating each color component signal for each horizontal line, based on a relational expression using an output value of a horizontal line, among output values of the image signals in a latest frame, a frame located one frame before the latest frame, and a frame located two frames before the latest frame, using each illumination period per one-line exposure period of each color in each frame, and using each exposure period of each color with respect to the horizontal line.

6 Claims, 20 Drawing Sheets

(58) Field of Classification Search
CPC ......... H04N 2005/2255; H04N 5/2354; H04N 5/2256; H04N 5/2353; H04N 5/3537; H04N 9/045; H04N 5/23203; H04N 5/3532; H04N 9/64; H04N 2209/043; H04N 2209/044; H04N 2209/049; H04N 9/07; A61B 1/00009; A61B 1/0005; A61B 1/0638; A61B 1/045; A61B 1/05; A61B 1/00006; A61B 1/043; A61B 1/06; A61B 1/0669; A61B 1/0684; A61B 1/00186; A61B 1/04; A61B 1/0661; A61B 1/07
See application file for complete search history.

(56) References Cited

FOREIGN PATENT DOCUMENTS

| | | | | |
|---|---|---|---|---|
| JP | 2014-183909 A | 10/2014 | | |
| WO | WO 2013/146311 A1 | 10/2013 | | |
| WO | WO 2013/157368 A1 | 10/2013 | | |
| WO | WO 2013146311 A1 * | 10/2013 | ......... | G02B 23/2461 |

OTHER PUBLICATIONS

Japanese Office Action dated Jul. 28, 2016 received in JP 2016-534264.

* cited by examiner

ENDOSCOPE SYSTEM

CROSS REFERENCES TO RELATED APPLICATIONS

This application is a continuation of PCT international application Ser. No. PCT/JP2016/050506, filed on Jan. 8, 2016 which designates the United States, incorporated herein by reference, and which claims the benefit of priority from Japanese Patent Application No. 2015-007078, filed on Jan. 16, 2015, incorporated herein by reference.

BACKGROUND

1. Technical Field

The disclosure relates to an endoscope system.

2. Related Art

In a medical field, endoscope systems have been conventionally used for in-vivo observation of a subject. In general, endoscopes capture in-vivo images as follows. An elongated flexible insertion portion is inserted into a subject such as a patient, illumination light supplied from a light source device is emitted from a distal end of the insertion portion, and reflected light of the illumination light is received by an imaging unit at the distal end of the insertion portion, and thereby an in-vivo image is captured. The in-vivo image thus captured by the imaging unit of the endoscope is subjected to a predetermined image process in a processing device of the endoscope system, and then displayed on a display of the endoscope system. A user such as a doctor observes an organ of the subject based on the in-vivo image displayed on the display.

There has been proposed technology in which a complementary metal oxide semiconductor (CMOS) sensor is applied as an image sensor included in such an endoscope system, and sequential irradiation is performed with blue light, green light, and red light as illumination light for an object, thereby sequentially generating imaging signals corresponding to the light of three colors (for example, see JP 2013-202189 A).

SUMMARY

In some embodiments, an endoscope system includes: a light source device configured to sequentially emit illumination light of three colors to irradiate an object in accordance with a predetermined cycle; an image sensor in which a plurality of pixels is arranged in a matrix, the plurality of pixels being configured to perform photoelectric conversion on light from the object irradiated with the illumination light to generate and output image signals; an illumination controller configured to cause the light source device to emit the illumination light of two of the three colors during a one-line exposure period of the image sensor; and a color component calculation unit configured to calculate each color component signal for each horizontal line, based on a relational expression using an output value of a horizontal line that is identical to a horizontal line to be calculated, among output values of the image signals in a latest frame, a frame located one frame before the latest frame, and a frame located two frames before the latest frame, using each illumination period per one-line exposure period of each color in each frame, and using each exposure period of each color with respect to the horizontal line to be calculated in each frame to be used for calculation.

In some embodiments, an endoscope system includes: a light source device configured to sequentially emit illumination light of three colors to irradiate an object in accordance with a predetermined cycle; an image sensor in which a plurality of pixels is arranged in a matrix, the plurality of pixels being configured to perform photoelectric conversion on light from the object irradiated with the illumination light to generate and output image signals; an illumination controller configured to cause the light source device to emit the illumination light of three colors in different illumination periods during a one-line exposure period of the image sensor; and a color component calculation unit configured to calculate each color component signal for each horizontal line, based on a relational expression using an output value of a horizontal line that is identical to a horizontal line to be calculated, among output values of the image signals in a latest frame, a frame located one frame before the latest frame, and a frame located two frames before the latest frame, using each illumination period per one-line exposure period of each color in each frame, and using each exposure period of each color with respect to the horizontal line to be calculated in each frame to be used for calculation.

The above and other features, advantages and technical and industrial significance of this invention will be better understood by reading the following detailed description of presently preferred embodiments of the invention, when considered in connection with the accompanying drawings.

DETAILED DESCRIPTION

Reference will be made below to an endoscope system as modes for carrying out the present invention (hereinafter referred to as "embodiment(s)"). The present invention is not limited by the embodiments. The same reference signs are used to designate the same elements throughout the drawings.

First Embodiment

Figure 1:
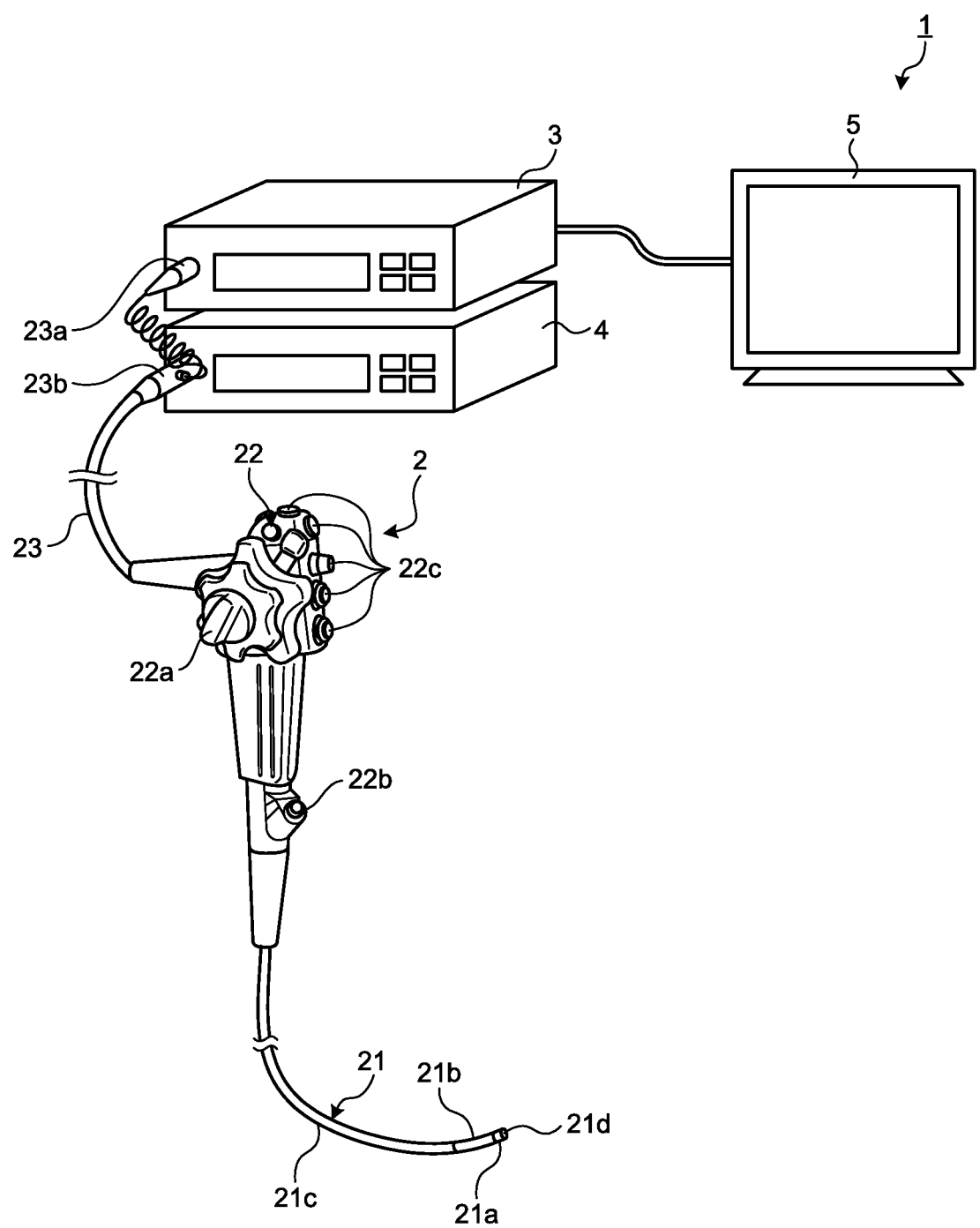
FIG. 1 is a schematic view illustrating an outline of a configuration of an endoscope system according to a first embodiment of the present invention.

FIG. 1 is a schematic diagram illustrating an outline of a configuration of an endoscope system according to a first embodiment of the present invention. As illustrated in FIG. 1, an endoscope system 1 according to the first embodiment includes an endoscope 2 (scope), a processing device 3 (signal processing device), a light source device 4, and a display device 5. The endoscope 2 (scope) is introduced into a subject to capture an in-vivo image of the subject and generate an in-vivo image signal of the subject. The processing device 3 (signal processing device), on which the endoscope 2 is detachably attached, performs a predetermined image process to the image signal transmitted from the endoscope 2, and controls each unit of the endoscope system 1. The light source device 4 generates illumination light (observation light) of the endoscope 2. The display device 5 displays an image corresponding to the image signal subjected to the image process by the processing device 3.

The endoscope 2 includes an insertion portion 21, an operating unit 22, and a universal cord 23. The insertion portion 21 is inserted into the subject. The operating unit 22 is located at a proximal-end side of the insertion portion 21 and grasped by an operator. The universal cord 23 is flexible and extends from the operating unit 22.

The insertion portion 21 is realized by using an illumination fiber (light-guide cable), an electric cable, and the like. The insertion portion 21 includes a distal end portion 21a, a bending portion 21b, and a flexible tube portion 21c. The distal end portion 21a includes an imaging unit having a CMOS image sensor therein as an image sensor which captures an in-vivo image of the subject. The bending portion 21b is constituted by a plurality of bending pieces and is bendable. The flexible tube portion 21c is provided at a proximal-end side of the bending portion 21b and is flexible. The distal end portion 21a includes an illumination unit for illuminating an inside of the subject through an illumination lens, an observation unit for capturing in-vivo images of the subject, an opening 21d for communicating with a treatment tool channel, and an air/water feeding nozzle (not illustrated).

The operating unit 22 includes a bending knob 22a, a treatment tool insertion portion 22b, and a plurality of switching units 22c. The bending knob 22a bends the bending portion 21b in upward and downward directions and left and right directions. Through the treatment tool insertion portion 22b, a treatment tool such as a biopsy forceps or a laser knife is inserted into a body cavity of the subject. With the plurality of switching units 22c, operations of peripheral devices such as the processing device 3, the light source device 4, an air feeding device, a water feeding device, and a gas feeding device are performed. The treatment tool inserted from the treatment tool insertion portion 22b comes out of the opening 21d at a distal end of the insertion portion 21 through the treatment tool channel provided inside.

The universal cord 23 is constituted by using an illumination fiber, an electric cable, and the like. The universal cord 23 includes connectors 23a and 23b which are branched at the proximal end and can be detachably attached to the processing device 3 and the light source device 4, respectively. The universal cord 23 transmits an image signal captured by the imaging unit provided in the distal end portion 21a to the processing device 3 via the connector 23a. The universal cord 23 transmits the illumination light emitted from the light source device 4 to the distal end portion 21a via the connector 23b, the operating unit 22, and the flexible tube portion 21c.

The processing device 3 performs a predetermined image process to an imaging signal of the inside of the subject captured by the imaging unit in the distal end portion 21a of the endoscope 2 and input via the universal cord 23. The processing device 3 controls each unit of the endoscope system 1 based on various kinds of instruction signals transmitted from the switching units 22c in the operating unit 22 of the endoscope 2 via the universal cord 23.

The light source device 4 is constituted by using a light source which emits light of a plurality of wavelength bands (colors), a condenser lens, and the like. The light source device 4 supplies light emitted from the light source to the endoscope 2 connected via the connector 23b and the illumination fiber of the universal cord 23, as illumination light used for illuminating inside the subject which is an object. The light source emits, for example, red (R) light, green (G) light, and blue (B) light.

The display device 5 is constituted by using a display which employs a liquid crystal or an organic electro-luminescence (EL), and the like. The display device 5 displays various kinds of information including an image corresponding to a display image signal subjected to the predetermined image process performed by the processing device 3 via a video cable. Consequently, the operator can observe a desired position inside the subject and determine a characteristic thereof by operating the endoscope 2 while viewing an image (in-vivo image) displayed by the display device 5.

Figure 2:
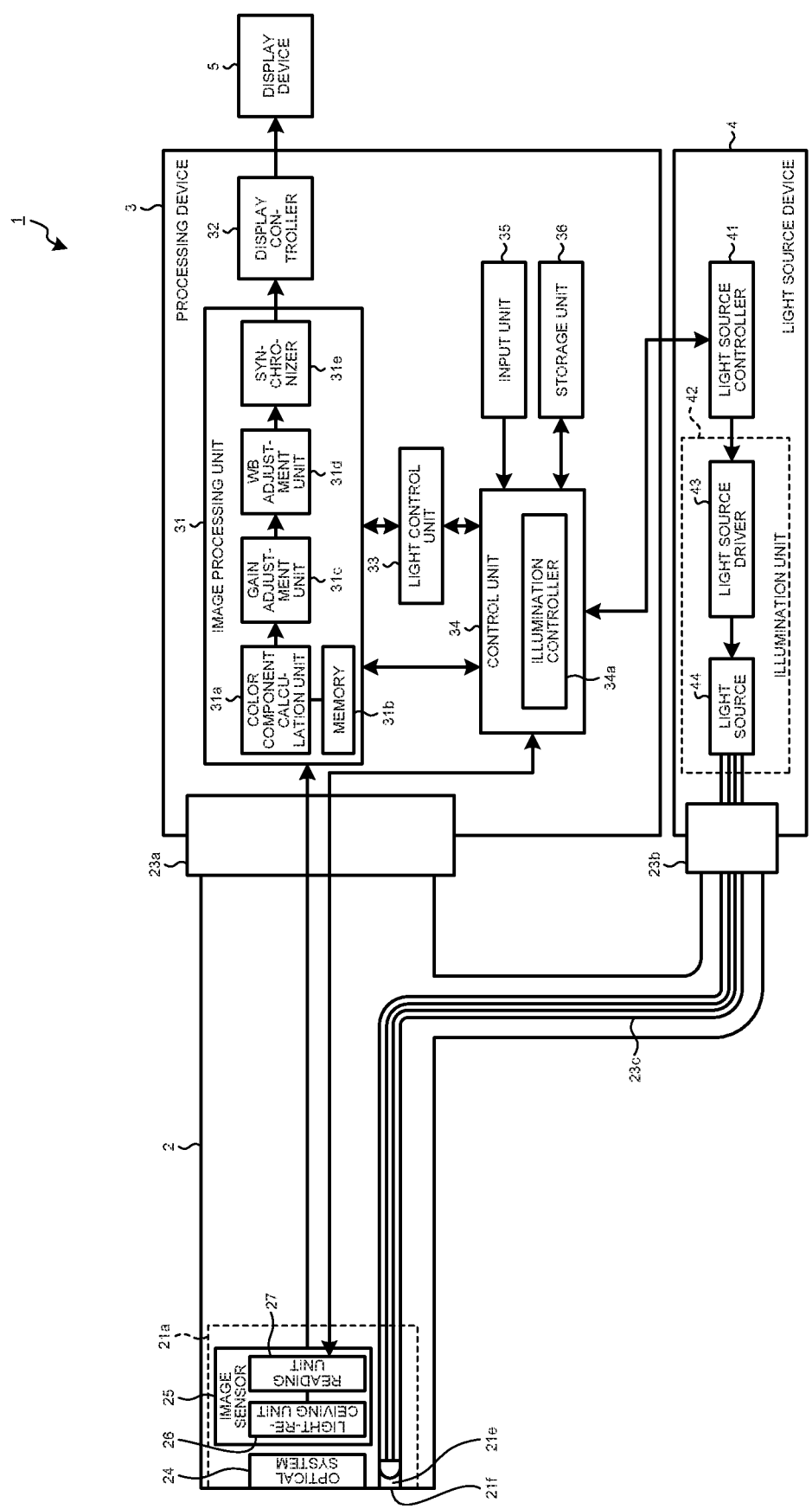
FIG. 2 is a block diagram schematically illustrating the configuration of the endoscope system illustrated in FIG. 1.

Then, the configuration of the endoscope system 1 described in FIG. 1 will be described. FIG. 2 is a block diagram schematically illustrating the configuration of the endoscope system 1 illustrated in FIG. 1.

The endoscope 2 includes an optical system 24 and an image sensor 25 at the distal end portion 21a. A distal end of a light-guide cable 23c which extends from the light source device 4 via the connector 23b is located at the distal end portion 21a. At the distal end of the light-guide cable 23c, an illumination lens 21e is provided. Light emitted from the light source device 4 travels via the light-guide cable 23c and the object is illuminated with the light from an illumination window 21f of the distal end portion 21a of the insertion portion 21.

The optical system 24 is constituted by using one or a plurality of lenses provided in front of the image sensor 25, and has an optical zoom function which changes an angle of view and a focus function which changes a focus.

The image sensor 25 includes a light-receiving unit 26 and a reading unit 27. The image sensor 25 is a CMOS image sensor capable of performing exposure and reading for each horizontal line.

In the light-receiving unit 26, a plurality of pixels is arranged in a matrix on a light-receiving surface. Each pixel receives light from the object irradiated with light, and photoelectrically converts the received light to generate a pixel signal (image signal). The optical system 24 is arranged on a light-receiving surface side of the light-receiving unit 26.

The reading unit 27 reads image signals generated by the plurality of pixels in the light-receiving unit 26. The reading unit 27 executes an imaging operation for performing exposure and reading from a top horizontal line, and generates an image signal by a rolling shutter method in which charge resetting, exposure, and reading are performed while shifting timing thereof for each horizontal line. Consequently, in the image sensor 25, each of exposure timing and reading timing is different for each horizontal line even when it is in one imaging period (frame). In other words, regarding a period during which a group of pixels in one horizontal line is exposed (one-line exposure period), although a time width is the same at any horizontal line, a start point and an end point are shifted for each horizontal line. The image signal read by the reading unit 27 is an electric signal (analog). The image sensor 25 includes an AFE unit (not illustrated) and a control unit (not illustrated). The AFE unit performs noise rejection, A/D conversion, or the like with respect to the electric signal of the image signal read by the reading unit 27. The control unit controls operations of the image sensor 25 in accordance with a control signal received from the processing device 3. The image signal (digital) generated by the image sensor 25 is output to the processing device 3 via a signal cable (not illustrated) or the connector 23a The processing device 3 includes an image processing unit 31, a display controller 32, a light control unit 33, a control unit 34, an input unit 35, and a storage unit 36.

The image processing unit 31 performs a predetermined image process to an image signal read by the reading unit 27 of the image sensor 25. The image processing unit 31 includes a color component calculation unit 31a, a memory 31b, a gain adjustment unit 31c, a white balance (WB) adjustment unit 31d, and a synchronizer 31e. The memory 31b is a rewritable memory capable of temporarily retaining an image signal read from the image sensor 25 on a per frame basis. The image processing unit 31 may perform an optical black subtraction process and an edge enhancement process.

The color component calculation unit 31a calculates each color component signal for each horizontal line using output values of, among image signals output from the image sensor 25 of the endoscope 2, image signals of a plurality of successive frames in accordance with the number of wavelength bands (colors) of illumination light. The color component calculation unit 31a calculates a color component signal of a line to be calculated using an output value of a line same as the line to be calculated among output values of image signals of the latest frame to which an image signal has been output from the image sensor 25 and of a frame before the latest frame. The color component calculation unit 31a calculates each color component signal for each horizontal line using a relational expression using each illumination period per time in the one-line exposure period of each color in each frame used for the calculation, and each exposure period of each color to a horizontal line to be calculated in each frame used for the calculation. In a case where illumination is performed with illumination light of three colors, i.e. R, G, and B, the color component calculation unit 31a generates, in three successive frames for each horizontal line, an R image signal when the light-receiving unit 26 receives only R light from the object irradiated with the R light, a G image signal when the light-receiving unit 26 receives only G light from the object irradiated with the G light, and a B image signal when the light-receiving unit 26 receives only B light from the object irradiated with the B light.

The gain adjustment unit 31c performs gain adjustment of R, G, and B image signals, which are color component signals of respective colors output from the color component calculation unit 31a, based on a gain adjustment value calculated by the light control unit 33 described later, and respective illumination periods of illumination light of three colors, i.e. R, G, and B, set by an illumination controller 34a described later.

The WB adjustment unit 31d adjusts white balance of the R, G, and B image signals, which are color component signals output from the color component calculation unit 31a.

The synchronizer 31e inputs each of the input R, G, and B image signals to a memory (not illustrated) provided for each pixel, makes the signals correspond to addresses of pixels of the light-receiving unit 26 read by the reading unit 27, retains a value of each memory while sequentially updating the value with each of the input image signals, and synchronizes respective image signals of the three memories as an RGB image signal.

The display controller 32 performs gradation conversion of the RGB image signal output from the image processing unit 31 in accordance with the display device 5, and generates a display image signal of which a format has been changed to a format corresponding to the display device 5, and outputs the display image signal to the display device 5. As a result, one in-vivo image is displayed on the display device 5.

The light control unit 33 detects a brightness level corresponding to each pixel from the image signal input to the image processing unit 31, and calculates a gain adjustment value for the image signal based on the detected brightness level. The light control unit 33 calculates, as a light control condition, a light irradiation amount of illumination light to be emitted next based on the detected brightness level. The light control unit 33 outputs the calculated gain adjustment value to the gain adjustment unit 31c, and outputs the light control condition with the detected brightness level to the control unit 34.

The control unit 34 is realized by using a CPU or the like. The control unit 34 controls a processing operation of each unit of the processing device 3. The control unit 34 controls operations of the processing device 3 by performing, for example, transmission of instruction information or data to each configuration of the processing device 3. The control unit 34 is connected to the image sensor 25 and the light source device 4 via cables, respectively, and controls the image sensor 25 and the light source device 4, as well. The control unit 34 includes an illumination controller 34a.

The illumination controller 34a sets an illumination period and an illumination intensity of each color in the light source device 4 based on the light control condition output from the light control unit 33. In the first embodiment, the illumination controller 34a sets the illumination intensity of illumination light to be constant, and then sets the illumination period. The illumination controller 34a sets driving conditions including an amount of a current supplied to each light source and a current supply period, and outputs a light source synchronization signal including a setting condition to the light source device 4. The illumination controller 34a sets a type, an amount, and illumination timing of light emitted by the light source device 4. The illumination controller 34a controls the light source device 4 to perform illumination with the illumination light for each exposure period in a top horizontal line 1 (one-line exposure period), for a period not exceeding the one-line exposure period. The illumination controller 34a sets irradiation time and an irradiation intensity on condition that an output value of the image sensor 25 is not saturated. The illumination controller 34a sets the irradiation time and the irradiation intensity with which the output value of the image sensor 25 is not saturated yet, and the gain adjustment unit 31c may perform gain adjustment of an image signal with a negative gain.

The input unit 35 is realized by using an operation device such as a mouse, a keyboard, and a touch panel, and receives input of various kinds of instruction information of the endoscope system 1. Specifically, the input unit 35 receives input of subject information (for example, an ID, a date of birth, and a name), identification information of the endoscope 2 (for example, an ID, and testing items), and various kinds of instruction information, for example, testing content.

The storage unit 36 is realized by using a volatile memory or non-volatile memory, and stores various programs for operating the processing device 3 and the light source device 4. The storage unit 36 temporarily stores information being processed by the processing device 3. The storage unit 36 stores an image signal read by the reading unit 27. The storage unit 36 stores an image signal processed in the image processing unit 31.

The light source device 4 includes a light source controller 41, and an illumination unit 42 provided with a light source driver 43 and a light source 44.

The light source controller 41 controls an illumination process of illumination light of the light source 44 under control of the illumination controller 34a. The light source driver 43 of the illumination unit 42 supplies predetermined power to the light source 44 under control of the light source controller 41. The light source 44 of the illumination unit 42 emits light of a plurality of wavelength bands (colors) as illumination light to be supplied to the endoscope 2. The light source 44 is constituted, for example, by using light sources of a red LED, a green LED, a blue LED and the like, and an optical system such as a condenser lens, and emits light of wavelength bands of R, G, and B (for example, R: 600 nm to 700 nm, G: 500 nm to 600 nm, and B: 400 nm to 500 nm). The light emitted from the light source 44 travels through the light-guide cable 23c, via the connector 23b and the universal cord 23, and the object is illuminated with the light from the illumination window 21f via the illumination lens 21e at the distal end portion 21a of the insertion portion 21. The image sensor 25 is arranged in the vicinity of the illumination window 21f. The light source 44 may be a combination of a white LED, and a rotating filter including a red filter, a green filter, and a blue filter which transmit light having wavelength bands of the R light, the G light, and the B light, respectively.

Figure 3:
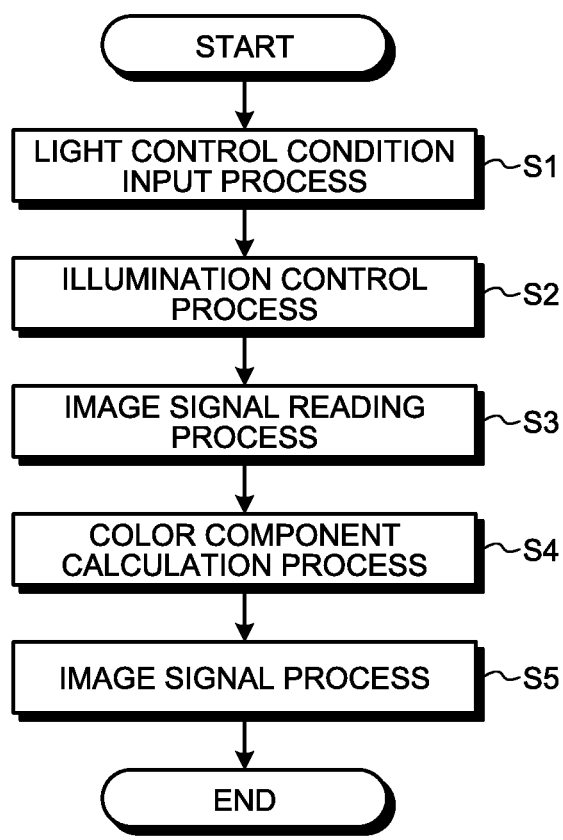
FIG. 3 is a flowchart illustrating a processing procedure of a process until an RGB image signal of one frame is generated in a processing device illustrated in FIG. 2.

FIG. 3 is a flowchart illustrating a processing procedure of a process until an RGB image signal of one frame is generated in the processing device 3. As illustrated in FIG. 3, first, a light control condition input process is performed in which a light control condition of illumination light to be used for next irradiation is input to the illumination controller 34a of the control unit 34 from the light control unit 33 (Step S1). The illumination controller 34a performs an illumination control process in which an illumination condition of the illumination light to be used for next irradiation is set in accordance with the input light control condition, and the light source device 4 is caused to perform illumination with illumination light on the set illumination condition (Step S2). The illumination controller 34a sets an illumination intensity of illumination light of any color to be constant, and then sets a color and an illumination period of the illumination light to be used for next irradiation. Together therewith, the control unit 34 performs an image signal reading process in which the image sensor 25 of the endoscope 2 is caused to sequentially execute, from a top horizontal line, an image signal reading process in which exposure and reading of an image signal are performed (Step S3).

The color component calculation unit 31a of the image processing unit 31 performs a color component calculation process in which each color component signal is calculated for each horizontal line using output values of image signals of a plurality of successive frames including image signals output from the image sensor 25 (Step S4). The color component calculation unit 31a calculates each color component signal with respect to all horizontal lines and outputs each color component signal on a per frame basis. Thereafter, the image processing unit 31 performs an image signal process in which a gain adjustment process, a white balance adjustment process, and a synchronization process are performed to each color component signal output by the color component calculation unit 31a to generate an RGB image signal of one frame (Step S5). The image processing unit 31 may perform in Step S5 an image signal process such as the optical black subtraction process and the edge enhancement process.

Figure 4:
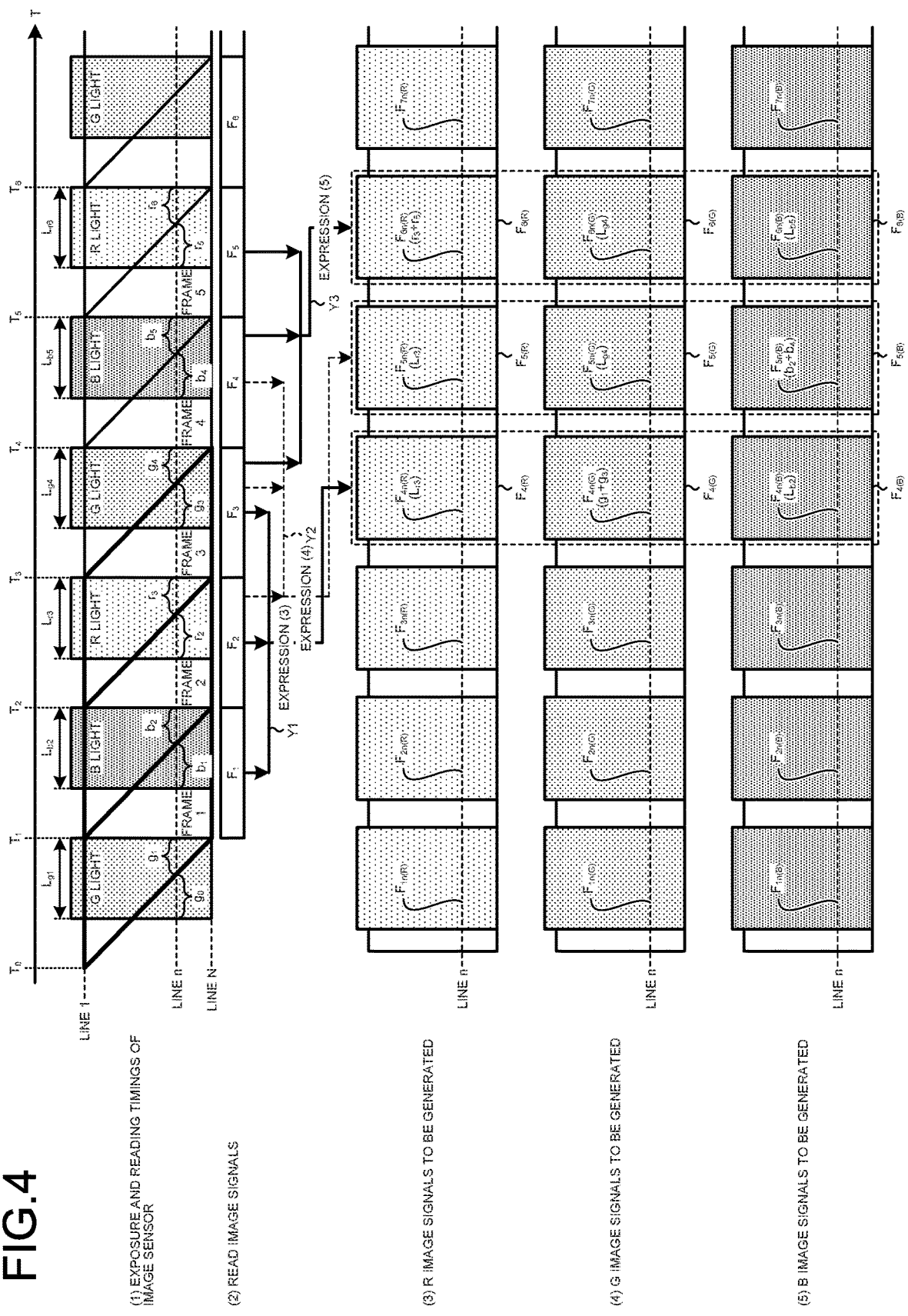
FIG. 4 is a timing chart illustrating exposure and reading timings in an image sensor illustrated in FIG. 2.

Next, each process illustrated in FIG. 3 will be described with reference to FIG. 4. FIG. 4 is a timing chart illustrating exposure and reading timings in the image sensor 25 illustrated in FIG. 2. FIG. 4 also illustrates image signals ((2) of FIG. 4) read from the image sensor 25 in accordance with to the exposure and reading timings of the image sensor 25 ((1) of FIG. 4, and R, G, and B image signals generated based on the image signals ((3) to (5) of FIG. 4). In (3) to (5) of FIG. 4, timing for generating an image signal of each color component is illustrated to be shifted from actual timing for ease of description of an image signal used for generating the image signal of each color component.

The illumination controller 34a performs an illumination control process in which the light source device 4 is caused to sequentially execute, based on the light control condition input in Step S1, an illumination process in which illumination with one of the R light, the G light, and the B light is performed for a period not exceeding the one-line exposure period in the one-line exposure period (Step S2). The illumination controller 34a causes light of any color to be turned off at the same timing as termination timing of the one-line exposure period of each frame in the image sensor 25. The illumination controller 34a adjusts illumination start time in accordance with the light control condition in each one-line exposure period. In the example in FIG. 4, the illumination controller 34a causes the light source device 4 to sequentially perform illumination with the G light, the B light and the R light in this order, for each one-line exposure period, and to turn off any light at termination time of the one-line exposure period of each frame.

Specifically, in a one-line exposure period (time $T_0$ to $T_1$) of frame 1, a period $L_{g1}$ is an illumination period of the G light; in a one-line exposure period (time $T_1$ to $T_2$) of frame 2, a period $L_{b2}$ is an illumination period of the B light; in a one-line exposure period (time $T_2$ to $T_3$) of frame 3, a period $L_{r3}$ is an illumination period of the R light; in a one-line exposure period (time $T_3$ to $T_4$) of frame 4, a period $L_{g4}$ is an illumination period of the G light; and in a one-line exposure period (time $T_4$ to $T_5$) of frame 5, a period $L_{b5}$ is an illumination period of the B light. The light source device 4 turns off, in any frame, each type of light at termination time $T_1$, $T_2$, $T_3$, $T_4$, or $T_5$ of the one-line exposure period of each frame.

Next, the image signal reading process (Step S3) in FIG. 3 will be described. The endoscope system 1 adopts, as the image sensor 25, a CMOS image sensor to which a rolling shutter method is applied in which exposure timing and reading timing are shifted for each horizontal line, and performs exposure and reading while shifting timing thereof in a time direction for each horizontal line.

Specifically, in the example in (1) of FIG. 4, regarding the top horizontal line 1 in frame 1, exposure is performed from time $T_0$ to $T_1$, and then a pixel signal is read at time $T_1$. Regarding pixels in subsequent horizontal lines, exposure and reading are performed while shifting timing thereof in a time direction for each horizontal line. Consequently, in frame 1, pixel signals of respective horizontal lines are read between time $T_1$ and $T_2$ in order from the top, and thereby an image signal $F_1$ of frame 1 is output (see (2) of FIG. 4). In frame 2, pixel signals of respective horizontal lines are read between time $T_2$ and $T_3$ in order, and thereby an image signal $F_2$ of frame 2 is output. Similarly, in frame 3, an image signal $F_3$ of frame 3 is output by a reading process between time $T_3$ and $T_4$; in frame 4, an image signal $F_4$ of frame 4 is output by a reading process between time $T_4$ and $T_5$; and in frame 5, an image signal $F_5$ of frame 5 is output by a reading process between time $T_5$ and $T_6$.

As described above, since exposure timing and reading timing are different for each horizontal line in the image sensor 25, each of output values of image signals $F_1$ to $F_5$ of respective frames is a value corresponding to exposure of light of a plurality of colors in accordance with variations in colors of light to be used for illumination, the number of illumination times, and illumination periods, depending on horizontal lines. The R light, the G light, and the B light are controlled to be sequentially used for illumination one by one for each one-line exposure period of each frame, and therefore, the exposure periods of the R light, the G light, and the B light are dispersed over three successive frames. Accordingly, in the color component calculation process (Step S4) in FIG. 3, the color component calculation unit 31a obtains a signal of a color component to be acquired by extracting the signal of the color component to be acquired from image signals of three successive frames including the latest frame to which an image signal has been output from the image sensor 25, while taking into consideration, for each horizontal line, a relationship between illumination periods of respective colors per a one-line exposure period in each frame of three successive frames and exposure periods of respective colors to a horizontal line to be calculated in each frame. It is assumed that the object is not in motion. The image signals of a plurality of frames used for calculation by the color component calculation unit 31a are temporarily retained in the memory 31b.

In the first embodiment, a simultaneous linear equation with three unknowns (expression (1)) holds which indicates a relationship among values of output image signals $F_{(k-3)n}$, $F_{(k-2)n}$, and $F_{(k-1)n}$ of a horizontal line n in successive frames (k-3) to (k-1), a matrix $A_k$ based on illumination periods of respective colors in each one-line exposure period of the successive frames (k-3) to (k-1) and exposure periods of respective colors to the horizontal line n in the frames (k-3) to (k-1), and an R image signal $F_{kn(R)}$, a G image signal $F_{kn(G)}$, and a B image signal $F_{kn(B)}$ of the horizontal line n in a calculated frame k.

$$A_k \begin{bmatrix} F_{kn(R)} \\ F_{kn(G)} \\ F_{kn(B)} \end{bmatrix} = \begin{bmatrix} F_{(k-1)n} \\ F_{(k-2)n} \\ F_{(k-3)n} \end{bmatrix} \quad (1)$$

Therefore, in order to obtain the R image signal $F_{kn(R)}$, the G image signal $F_{kn(G)}$, and the B image signal $F_{kn(B)}$ of the horizontal line n in the calculated frame k, Expression (2) obtained by modifying Expression (1) is solved to obtain an inverse matrix $A_k^{-1}$ of Expression (2). In other words, the color component calculation unit 31a calculates each color component signal of a line to be calculated by applying, to Expression (2), an output value of a line same as the line to be calculated among output values of image signals in the latest frame to which an image signal has been output from the image sensor 25, and in a frame located one frame before the latest frame and in a frame located two frames before the latest frame.

$$\begin{bmatrix} F_{kn(R)} \\ F_{kn(G)} \\ F_{kn(B)} \end{bmatrix} = A_k^{-1} \begin{bmatrix} F_{(k-1)n} \\ F_{(k-2)n} \\ F_{(k-3)n} \end{bmatrix} \quad (2)$$

For example, an R image signal $F_{4n(R)}$, a G image signal $F_{4n(G)}$, and a B image signal $F_{4n(B)}$ of the horizontal line n in a fourth frame are obtained by inputting, to Expression (3) below, output values of the horizontal line n in image signals $F_{1n}$, $F_{2n}$, and $F_{3n}$ of frames 1 to 3 (see an arrow Y1) In Expression (3), parameters of a matrix $A_4$ are illumination periods $L_{b2}$ and $L_{r3}$ of the B light and the R light in respective one-line exposure periods in successive frames 2 and 3, as well as exposure periods $g_1$ and $g_3$ of the G light, exposure periods $b_1$ and $b_2$ of the B light, and exposure periods $r_2$ and $r_3$ of R light, to the horizontal line n in frames 1 to 3.

$$\begin{bmatrix} \frac{r_3}{L_{r3}} & \frac{g_3}{g_1+g_3} & 0 \\ \frac{r_2}{L_{r3}} & 0 & \frac{b_2}{L_{b2}} \\ 0 & \frac{g_1}{g_1+g_3} & \frac{b_1}{L_{b2}} \end{bmatrix} \begin{bmatrix} F_{4n(R)} \\ F_{4n(G)} \\ F_{4n(B)} \end{bmatrix} = \begin{bmatrix} F_{3n} \\ F_{2n} \\ F_{1n} \end{bmatrix} \quad (3)$$

The color component calculation unit 31a performs a calculation process to solve Expression (3) to which the exposure periods $r_2$ and $r_3$ of the R light, the exposure periods $g_1$ and $g_3$ of the G light, and the exposure periods $b_1$ and $b_2$ of the B light, each of which corresponding to the horizontal line n, have been applied as the parameters of the matrix $A_4$, and output values of the horizontal line n of the image signals $F_{3n}$, $F_{2n}$, and $F_{1n}$ have been input. As a result, the color component calculation unit 31a can generate the R image signal $F_{4n(R)}$ corresponding to an image signal in a case where exposure has been performed with the R light for an illumination period $L_{r3}$, the G image signal $F_{4n(G)}$ corresponding to an image signal in a case where exposure has been performed with the G light for a period $(g_1+g_3)$, and the B image signal $F_{4n(B)}$ corresponding to an image signal in a case where exposure has been performed with the B light for an illumination period $L_{b2}$, each of which corresponding to the horizontal line n in the fourth frame. The color component calculation unit 31a sequentially performs calculation processes to solve Expression (3) in which parameters corresponding to each horizontal line are used as parameters of the matrix $A_4$, and to which output values of the image signals $F_{3n}$, $F_{2n}$, and $F_{1n}$ of the horizontal line n to be calculated have been input, from the top horizontal line 1 to a last horizontal line N, respectively. As a result, an R image signal $F_{4(R)}$, a G image signal $F_{4(G)}$, and a B image signal $F_{4(B)}$ of the fourth frame can be acquired on a per frame basis. Hereinafter, a row vector $(r_3/L_{r3}, g_3/(g_1+g_3), 0)$ constituted by components in a first row of the matrix $A_4$ in Expression (3) is denoted by Ra, a row vector $(r_2/L_{r3}, 0, b_2/L_{b2})$ constituted by components in a second row thereof is denoted by Rb, and a row vector $(0, g_1/(g_1+g_3), b_1/L_{b2})$ constituted by components in a third row thereof is denoted by Rc.

An R image signal $F_{5n(R)}$, a G image signal $F_{5n(G)}$, and a B image signal $F_{5n(B)}$ of the horizontal line n in a fifth frame are obtained by inputting, to Expression (4) below, output values of the horizontal line n in image signals $F_{2n}$, $F_{3n}$, and $F_{4n}$ of frames 2 to 4 (see an arrow Y2). In Expression (4), parameters of a matrix $A_5$ are illumination periods $L_{r3}$ and $L_{g4}$ of the R light and the G light in respective one-line exposure periods in successive frames 3 and 4, as well as exposure periods $r_2$ and $r_3$ of the R light, exposure periods $g_3$ and $g_4$ of the G light, and exposure periods $b_2$ and $b_4$ of the B light, to the horizontal line n in frames 2 to 4.

$$\begin{bmatrix} 0 & \frac{g_4}{L_{g4}} & \frac{b_4}{b_2+b_4} \\ \frac{r_3}{L_{r3}} & \frac{g_3}{L_{g4}} & 0 \\ \frac{r_2}{L_{r3}} & 0 & \frac{b_2}{b_2+b_4} \end{bmatrix} \begin{bmatrix} F_{5n(R)} \\ F_{5n(G)} \\ F_{5n(B)} \end{bmatrix} = \begin{bmatrix} F_{4n} \\ F_{3n} \\ F_{2n} \end{bmatrix} \quad (4)$$

The color component calculation unit 31a performs a calculation process to solve Expression (4) to which the exposure periods $r_2$ and $r_3$ of the R light, the exposure periods $g_3$ and $g_4$ of the G light, and the exposure periods $b_2$ and $b_4$ of the B light, each of which corresponding to the horizontal line n, have been applied as the parameters of the matrix $A_5$, and output values of the horizontal line n of the image signals $F_{4n}$, $F_{3n}$, and $F_{2n}$ have been input. As a result, the color component calculation unit 31a can generate the R image signal $F_{5n(R)}$ corresponding to an image signal in a case where exposure has been performed with the R light for an illumination period $L_{r3}$, the G image signal $F_{5n(G)}$ corresponding to an image signal in a case where exposure has been performed with the G light for an illumination period $L_{g4}$, and the B image signal $F_{5n(B)}$ corresponding to an image signal in a case where exposure has been performed with the B light for a period $(b_2+b_4)$, each of which corresponding to the horizontal line n in the fifth frame. The color component calculation unit 31a sequentially performs calculation processes to solve Expression (4) in which parameters corresponding to each horizontal line are used as parameters of the matrix $A_5$, and to which output values of the image signals $F_{4n}$, $F_{3n}$, and $F_{2n}$ of the horizontal line to be calculated have been input, from the top horizontal line 1 to the last horizontal line N, respectively. As a result, an R image signal $F_{5(R)}$, a G image signal $F_{5(G)}$, and a B image signal $F_{5(B)}$ of the fifth frame can be acquired on a per frame basis.

An R image signal $F_{6n(R)}$, a G image signal $F_{6n(G)}$, and a B image signal $F_{6n(B)}$ of the horizontal line n in a sixth frame are obtained by inputting, to Expression (5) below, output values of the horizontal line n in image signals $F_{3n}$, $F_{4n}$, and $F_{5n}$ of frames 3 to 5 (see an arrow Y3). In Expression (5), parameters of a matrix $A_6$ are illumination periods $L_{g4}$ and $L_{b5}$ of the G light and the B light in respective one-line exposure periods in successive frames 4 and 5, as well as exposure periods $r_3$ and $r_5$ of the R light, exposure periods $g_3$ and $g_4$ of the G light, and exposure periods $b_4$ and $b_5$ of the B light, to the horizontal line n in frames 3 to 5.

$$\begin{bmatrix} \frac{r_5}{r_3+r_5} & 0 & \frac{b_5}{L_{b5}} \\ 0 & \frac{g_4}{L_{g4}} & \frac{b_4}{L_{b5}} \\ \frac{r_3}{r_3+r_5} & \frac{g_3}{L_{g4}} & 0 \end{bmatrix} \begin{bmatrix} F_{6n(R)} \\ F_{6n(G)} \\ F_{6n(B)} \end{bmatrix} = \begin{bmatrix} F_{5n} \\ F_{4n} \\ F_{3n} \end{bmatrix} \quad (5)$$

The color component calculation unit 31a performs a calculation process to solve Expression (5) to which the exposure periods $r_3$ and $r_5$ of the R light, the exposure periods $g_3$ and $g_4$ of the G light, and the exposure periods $b_4$ and $b_5$ of the B light, each of which corresponding to the horizontal line n, have been applied as the parameters of the matrix $A_6$, and output values of the horizontal line n of the image signals $F_{5n}$, $F_{4n}$, and $F_{3n}$ have been input. As a result, the color component calculation unit 31a can generate the R image signal $F_{6n(R)}$ corresponding to an image signal in a case where exposure has been performed with the R light for an illumination period $(r_3+r_5)$, the G image signal $F_{6n(G)}$ corresponding to an image signal in a case where exposure has been performed with the G light for an illumination period $L_{g4}$, and the B image signal $F_{6n(B)}$ corresponding to an image signal in a case where exposure has been performed with the B light for an illumination period $L_{b5}$, each of which corresponding to the horizontal line n in the sixth frame. The color component calculation unit 31a sequentially performs calculation processes to solve Expression (5) in which parameters corresponding to each horizontal line are used as parameters of the matrix $A_6$, and to which output values of the image signals $F_{5n}$, $F_{4n}$, and $F_{3n}$ of the horizontal line to be calculated have been input, from the top horizontal line 1 to the last horizontal line N, respectively. As a result, an R image signal $F_{6(R)}$, a G image signal $F_{6(G)}$, and a B image signal $F_{6(B)}$ of the sixth frame can be acquired on a per frame basis.

Regarding a seventh frame and subsequent frames, an image signal of each color component of each horizontal line n may be calculated sequentially using Expressions (3) to (5) on a per three-frame basis. Regarding the matrix $A_k$ of Expressions (3) to (5), by adding 3 to a frame number of each parameter, and calculating the inverse matrix $A_k^{-1}$ of the matrix $A_k$ for each horizontal line n, the image signal of each color component is acquired for each horizontal line n.

Figure 5:
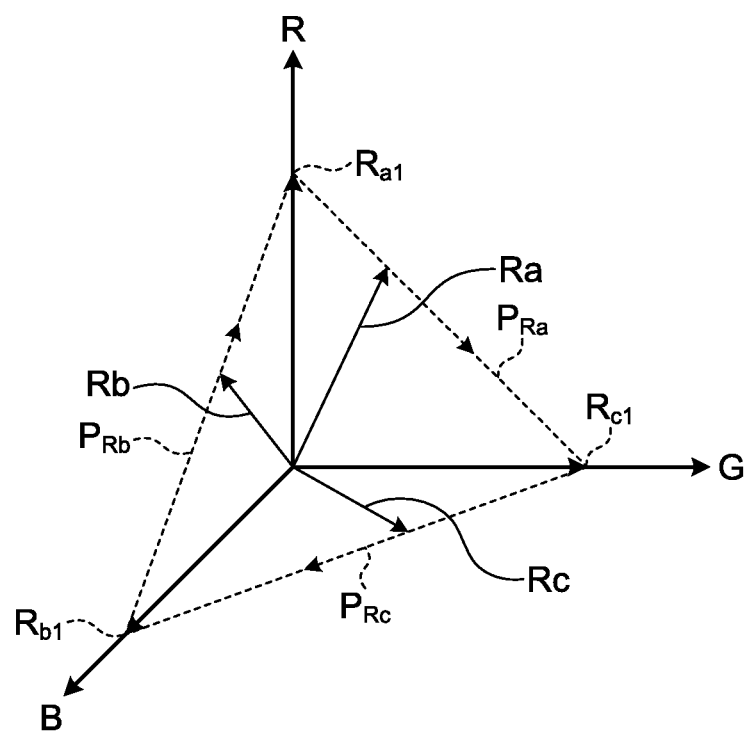
FIG. 5 is a diagram explaining uniqueness of a solution of image signals obtained in the first embodiment.

A rank of the matrix $A_k$ in relational expressions used in the first embodiment will be described. FIG. 5 is a diagram explaining uniqueness of a solution of image signals obtained in the first embodiment, and illustrating a case where the row vectors Ra, Rb, and Rc of Expression (3) are viewed in an RGB space. The row vector Ra is a vector on an R-G plane, and depicts a locus $P_{Ra}$ starting from a position $R_{a1}$ corresponding to the horizontal line 1 and progressing toward a position $R_{c1}$ with increasing line number. The row vector Rb is a vector on a B-R plane, and depicts a locus $P_{Rb}$ starting from a position $R_{b1}$ corresponding to the horizontal line 1 and progressing toward a position $R_{a1}$ with increasing line number. The row vector Rc is a vector on a G-B plane, and depicts a locus $P_{Rc}$ starting from a position $R_{c1}$ corresponding to the horizontal line 1 and progressing toward a position $R_{b1}$ with increasing line number. These row vectors Ra, Rb, and Rc respectively depict, as in FIG. 5, loci $P_{Ra}$, $P_{Rb}$, and $P_{Rc}$ different from one another on respective planes of the R-G plane, the B-R plane, and the G-B plane. Therefore, regarding any of the row vectors Ra to Rc, any two row vectors do not overlap on an R axis, a G axis, or a B axis simultaneously.

Consequently, since the row vectors Ra to Rc are always linearly independent, the rank of the matrix $A_k$ is 3, and the solution of Expression (3) is unique. Consequently, since the solution of Expression (3) is unexceptionally unique in both cases where the illumination periods of R, G, and B are the same, and where the illumination periods thereof are different, a value of each of the R image signal $F_{4n(R)}$, the G image signal $F_{4n(G)}$, and the B image signal $F_{4n(B)}$ can be obtained through calculation. Since the same holds for Expressions (4) and (5), a color component signal can be obtained uniquely for any frame.

In the above color component calculation process (Step S4), all of the R, G, and B image signals are calculated as color component signals in one frame, and in the image signal process (Step S5), a predetermined image signal process is executed to these R, G, and B image signals. In the synchronization process in the above process, the synchronizer 31e adopts, among the R, G, and B image signals, an image signal of a color used for exposure in an exposure period closest to a reading period of the last frame of the three successive frames used for the calculation. Then, the synchronization process is performed based on the image signal of the color thus adopted, one color in each frame, on a per three-frame basis. For example, in the fourth frame, the R image signal $F_{4(R)}$ corresponding to the exposure period $L_{r3}$ closest to the reading period $T_3$ to $T_4$ in frame 3 is adopted; in the fifth frame, the G image signal $F_{5(G)}$ corresponding to the exposure period $L_{g4}$ closest to the reading period $T_4$ to $T_5$ in frame 4 is adopted; and in the sixth frame, the B image signal $F_{6(B)}$ corresponding to the exposure period $L_{b5}$ closest to the reading period $T_5$ to $T_6$ in frame 5 is adopted. The synchronization process is performed using the adopted R image signal $F_{4(R)}$, G image signal $F_{5(G)}$, and B image signal $F_{6(B)}$ to generate an RGB image signal. The synchronizer 31e may use, as a matter of course, the R, G, and B image signals of the same frame to perform the synchronization process, and generate the RGB image signal for one frame each.

As described above, in the first embodiment, an image signal of each color component of a frame to be acquired is extracted for each horizontal line through calculation using output values of image signals of a plurality of successive frames, in the color component calculation unit 31a in the processing device 3. Consequently, according to the first embodiment, it is possible to freely set an exposure period of each illumination light in a one-line exposure period, which makes it possible to secure a sufficient exposure period for all pixels and to maintain the sensitivity of the image sensor 25. In addition, in the first embodiment, the color component calculation unit 31a extracts an image signal of each color component of a frame to be acquired through a calculation process, and thus there is no need to provide a period (V-blank period) during which exposure is commonly performed for all horizontal lines. Consequently, it is possible to sufficiently secure a signal transmission period, as well. Consequently, according to the first embodiment, it is possible to sufficiently secure an exposure period for all pixels while suppressing a cable transmission load.

First Modification of First Embodiment

The first embodiment can be applied not only to a sequential lighting method, but also to, for example, a narrow band imaging (NBI) observation method. In the sequential lighting method, illumination light of three colors of R, G, and B is sequentially switched, and in the NBI observation method, observation is performed using NBI illumination light of two types of bands, i.e. blue light and green light, the bandwidths thereof being narrowed so as to be easily absorbed by hemoglobin in the blood. In a case of the NBI observation method, the light source device 4 performs irradiation by sequentially switching between blue light (V light) with a narrowed bandwidth and G light with a narrowed bandwidth, in accordance with control of the illumination controller 34a. The wavelength band of the V light is, for example, wavelengths of 390 nm to 470 nm.

Figure 6:
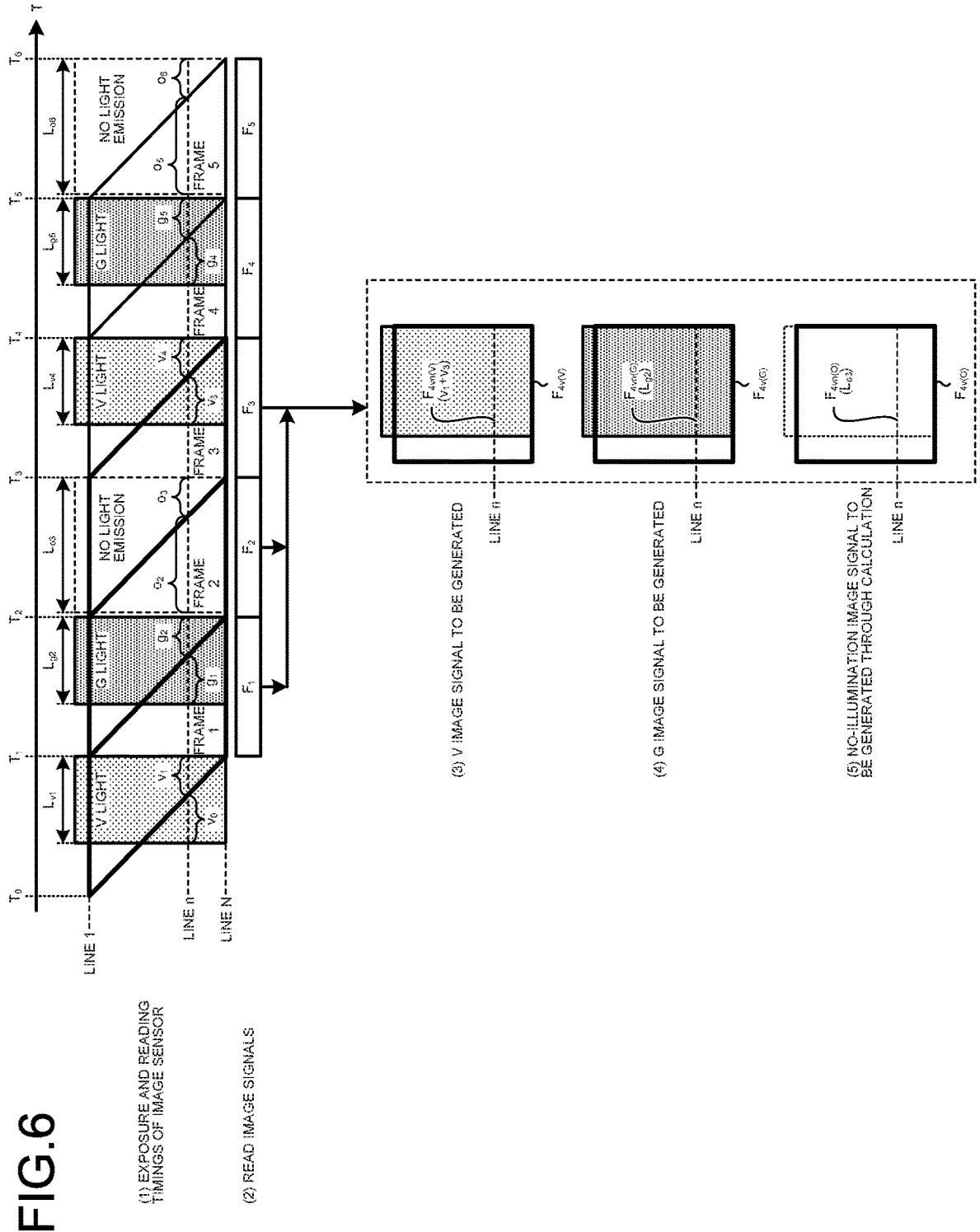
FIG. 6 is a timing chart illustrating exposure and reading timings in an image sensor in a first modification in the first embodiment when an NBI observation method is employed.

FIG. 6 is a timing chart illustrating exposure and reading timings in the image sensor 25 when the NBI observation method is employed. FIG. 6 also illustrates image signals ((2) of FIG. 6) read from the image sensor 25 in accordance with the exposure and reading timings of the image sensor 25 ((1) of FIG. 6), and V and G image signals, and the like generated based on the image signals ((3) to (5) of FIG. 6). In (3) to (5) of FIG. 6, timing for generating an image signal of each color component is illustrated to be shifted from actual timing for ease of description of an image signal used for generating the image signal of each color component. Also in that case, the processing device 3 generates the V image signal and the G image signal of one frame by performing substantially the same process as each process illustrated in FIG. 3.

First, the illumination controller 34a performs, based on a light control condition input in the light control condition input process (Step S1 in FIG. 3), an illumination control process (Step S2). Since the V light and the G light are used as irradiation light and the number of colors of light is reduced to two, in the NBI observation method, a no-light frame which emits no light is set in order to keep the rank of a determinant used in the calculation process at 3. Specifically, the illumination controller 34a causes the light source device 4 to perform irradiation with the V light in a one-line exposure period of frame 1, to perform irradiation with the G light in a one-line exposure period of frame 2, and in a one-line exposure period of subsequent frame 3, the no-light frame which emits no light is employed. Then, also in three successive frames, the illumination controller 34a repeats the illumination control including the V light irradiation (frame 4), the G light irradiation (frame 5), and no light emission (frame 6), on a per three-frame basis.

Subsequently, the color component calculation unit 31a generates the V image signal and the G image signal for each horizontal line by using image signals of the three successive frames read in the image signal reading process (Step S3) and a corresponding calculation expression among Expressions (3) to (5) described above (Step S4). For example, when generating the V image signal $F_{4v(V)}$ and the G image signal $F_{4v(G)}$ of the fourth frame, the color component calculation unit 31a inputs output values of the horizontal line n of the three successive frame image signals $F_1$ to $F_3$ (see (2) of FIG. 6) to Expression (3) for each horizontal line n. In that case, in the horizontal line n, parameters of the matrix $A_k$ of Expression (3) are illumination periods $L_{v1}$ and $L_{g2}$ of the V light and the B light in respective one-line exposure periods of successive frames 1 to 3, and exposure periods $v_1$ and $v_3$ of the V light and exposure periods $g_1$ and $g_2$ of the G light to the horizontal line n in frames 1 to 3, and in addition, an apparent illumination period $L_{o3}$ and apparent exposure periods $O_2$ and $O_3$ in frame 3 with no light emission.

Then, the color component calculation unit 31a generates, by solving Expression (3), a V image signal $F_{4vn(V)}$ ((3) of FIG. 6) corresponding to an image signal in a case where exposure has been performed with the V light for a period ($v_1+v_3$), a G image signal $F_{4vn(G)}$ ((4) of FIG. 6) corresponding to an image signal in a case where exposure has been performed with the G light for an illumination period $L_{g2}$, each of which corresponding to the horizontal line n in the fourth frame. As a result of the calculation, a no-illumination image signal $F_{4vn(O)}$ corresponding to the apparent illumination period $L_{O3}$ is also generated ((5) of FIG. 6). The color component calculation unit 31a sequentially performs calculation processes to solve Expression (3) in which parameters corresponding to each horizontal line are used as parameters of the matrix $A_k$, and to which output values of the image signals $F_{3n}$, $F_{2n}$, and $F_{1n}$ of the horizontal line to be calculated have been input, from the top horizontal line 1 to the last horizontal line N, respectively. As a result, a V image signal $F_{4V(V)}$, a G image signal $F_{4V(G)}$, and a no-illumination image signal $F_{4V(O)}$ of the fourth frame can be acquired on a per frame basis. Subsequently, the image processing unit 31 performs an image signal process (Step S5) including a gain adjustment process with respect to each of the V image signal $F_{4v(V)}$ and the G image signal $F_{4v(G)}$ calculated by the color component calculation unit 31a, and generates an NBI image signal. Here, in a case where the no-light frame is set, there is no need to control light, and therefore irradiation with the V light and the G light can be performed always for the longest irradiation time without light control. Accordingly, it is considered that calculation errors can be reduced, and an afterimage effect can also be reduced.

Figure 7:
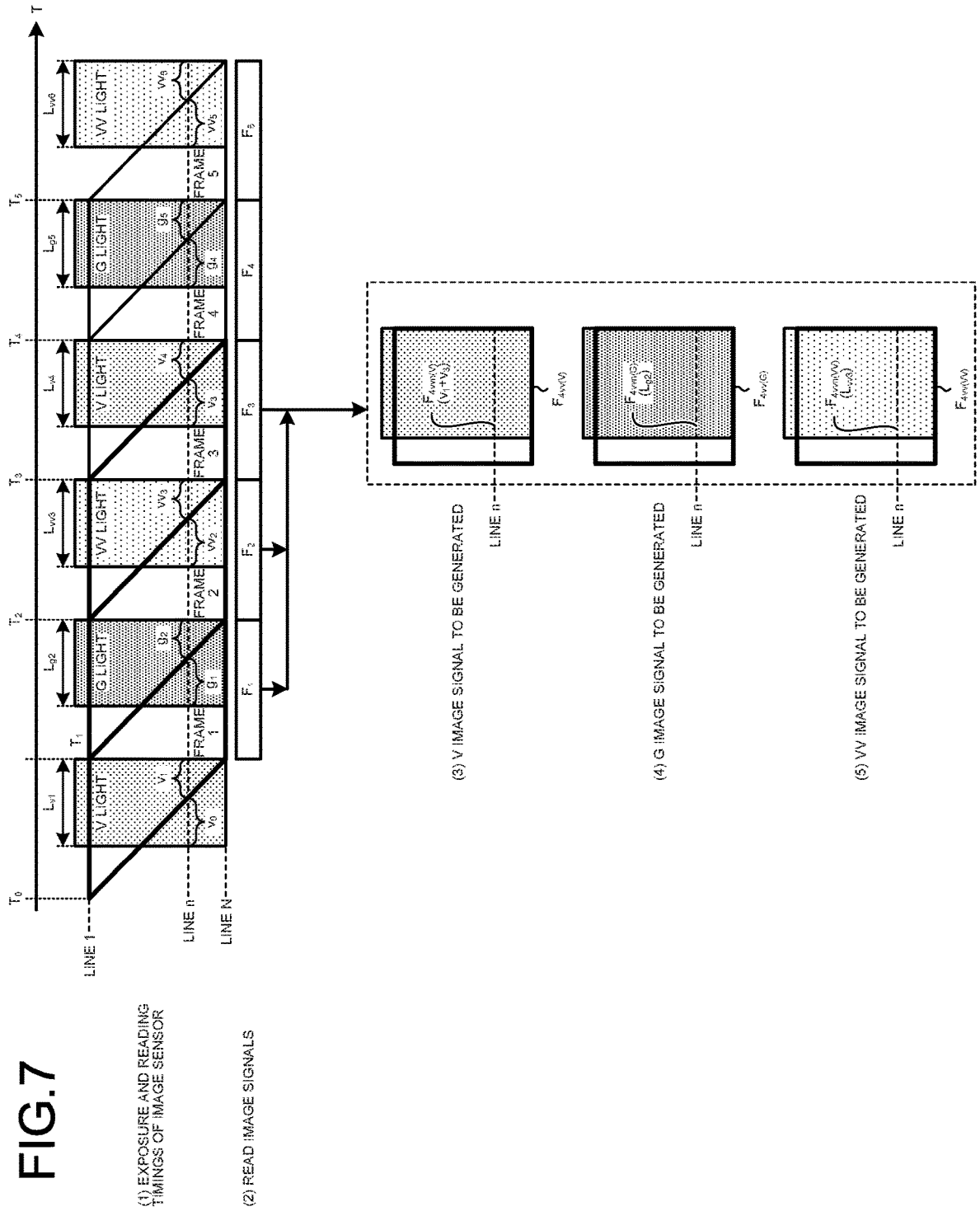
FIG. 7 is a timing chart illustrating another example of the exposure and reading timings in the image sensor in the first modification in the first embodiment when the NBI observation method is employed.

FIG. 7 is a timing chart illustrating other exposure and reading timings in the image sensor 25 when the NBI observation method is employed. The illumination controller 34a may cause the light source device 4 to perform, as illustrated in (1) of FIG. 7, irradiation with second V light (VV light) in frames 3 and 6 which are no-light frames in FIG. 6. In that case, regarding the horizontal line n in the fourth frame, parameters of the matrix $A_k$ of Expression (3) are illumination periods $L_{v1}$, $L_{g2}$, and $L_{vv3}$ of the V light, the G light, and the VV light in respective one-line exposure periods of successive frames 1 to 3, as well as exposure periods $v_1$ and $v_3$ of the V light, exposure periods $g_1$ and $g_2$ of the G light, and exposure periods $vv_2$ and $vv_3$ of the VV light to the horizontal line n in frames 1 to 3. The color component calculation unit 31a can generate a V image signal $F_{4vvn(V)}$ ((3) of FIG. 7) and a G image signal $F_{4vvn(G)}$ ((4) of FIG. 7) in the horizontal line n in the fourth frame, and in addition, a VV image signal $F_{4vvn(VV)}$ ((5) of FIG. 7) corresponding to an image signal in a case where exposure has been performed with the VV light for the illumination period $L_{vv3}$ by inputting, to Expression (3), output values of the horizontal line n of the frame image signals $F_1$ to $F_3$ (see (2) of FIG. 7) and solving Expression (3). The color component calculation unit 31a sequentially performs calculation processes to solve Expression (3) in which parameters corresponding to each horizontal line n are used as parameters of the matrix $A_k$, and to which output values of the image signals $F_{3n}$, $F_{2n}$, and $F_{1n}$ of the horizontal line n to be calculated have been input, from the top horizontal line 1 to the last horizontal line N, thereby acquiring a V image signal $F_{4vv(V)}$, a G image signal $F_{4vv(G)}$, and a VV image signal $F_{4vv(VV)}$ of the fourth frame on a per frame basis. Since sufficient sensitivity cannot be secured for the V light, a balance in the sensitivity between the V light image signal and the G light image signal is adjusted in that case by performing the V light illumination twice and using two V light image signals. It is also possible, as a matter of course, to perform the G light illumination twice other than to perform the V light illumination twice in three frames.

Second Modification of First Embodiment

Figure 8:
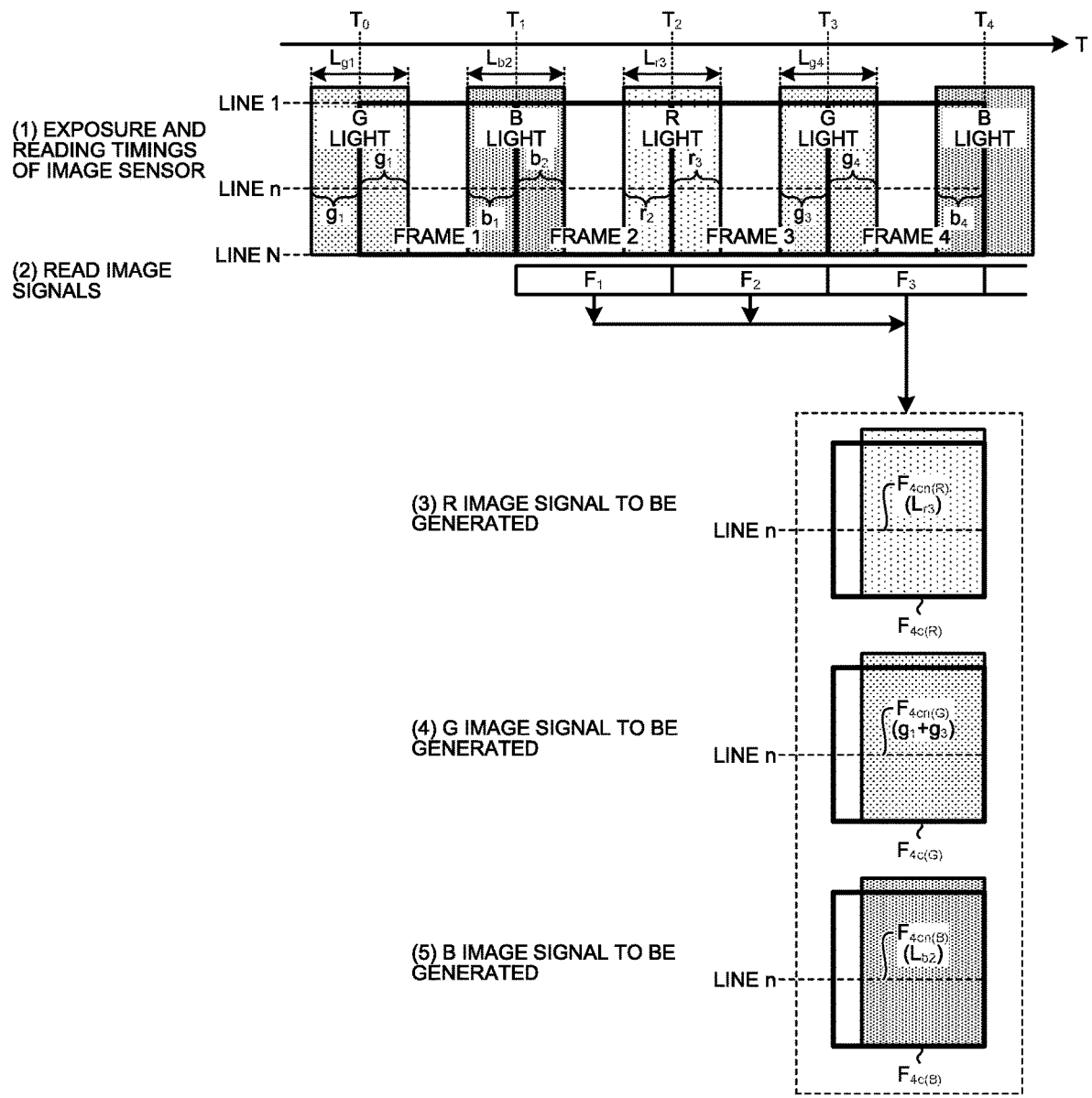
FIG. 8 is a timing chart illustrating exposure and reading timings in a case where the image sensor in the first embodiment is a CCD image sensor.

The first embodiment can be applied also to a case where the image sensor 25 is a CCD image sensor which adopts a global shutter method. FIG. 8 is a timing chart illustrating exposure and reading timings in a case where the image sensor 25 is a CCD image sensor.

As illustrated in (1) of FIG. 8, the illumination controller 34a causes the light source device 4 to sequentially perform irradiation with illumination light in order of the G light, the B light, and the R light. The image signal $F_1$ of frame 1 is read from the image sensor 25 at time $T_1$ in each B light irradiation period $L_{b2}$ for any of all horizontal lines. Similarly, the image signals $F_2$ and $F_3$ of frames 2 and 3 are read from the image sensor 25 at time $T_2$ and time $T_3$ in the R light irradiation period $L_{r3}$ and the G light irradiation period $L_{g4}$, respectively. In a case where the color component calculation unit 31a generates an R image signal $F_{4c(R)}$, a G image signal $F_{4c(G)}$, and a B image signal $F_{4c(B)}$ of the fourth frame, the color component calculation unit 31a sequentially performs, for each horizontal line, a calculation process in which an output value of a horizontal line to be calculated among the image signals $F_1$ to $F_3$ (see (2) of FIG. 8) of the three successive frames is input to solve Expression (3), from the top horizontal line 1 to the last horizontal line N, respectively. In that case, similarly to the first embodiment, in the horizontal line n, parameters of the matrix $A_k$ of Expression (3) are illumination periods $L_{r3}$ and $L_{b2}$ of the R light and the B light in respective one-line exposure periods of successive frames 1 to 3, as well as exposure periods $r_2$ and $r_3$ of the R light, exposure periods $g_1$ and $g_3$ of the G light, and exposure periods $b_1$ and $b_2$ of the B light to the horizontal line n in frames 1 to 3.

Second Embodiment

Next, a second embodiment will be described. In the second embodiment, a case will be described in which illumination is performed with illumination light of two of three colors in one one-line exposure period.

Figure 9:
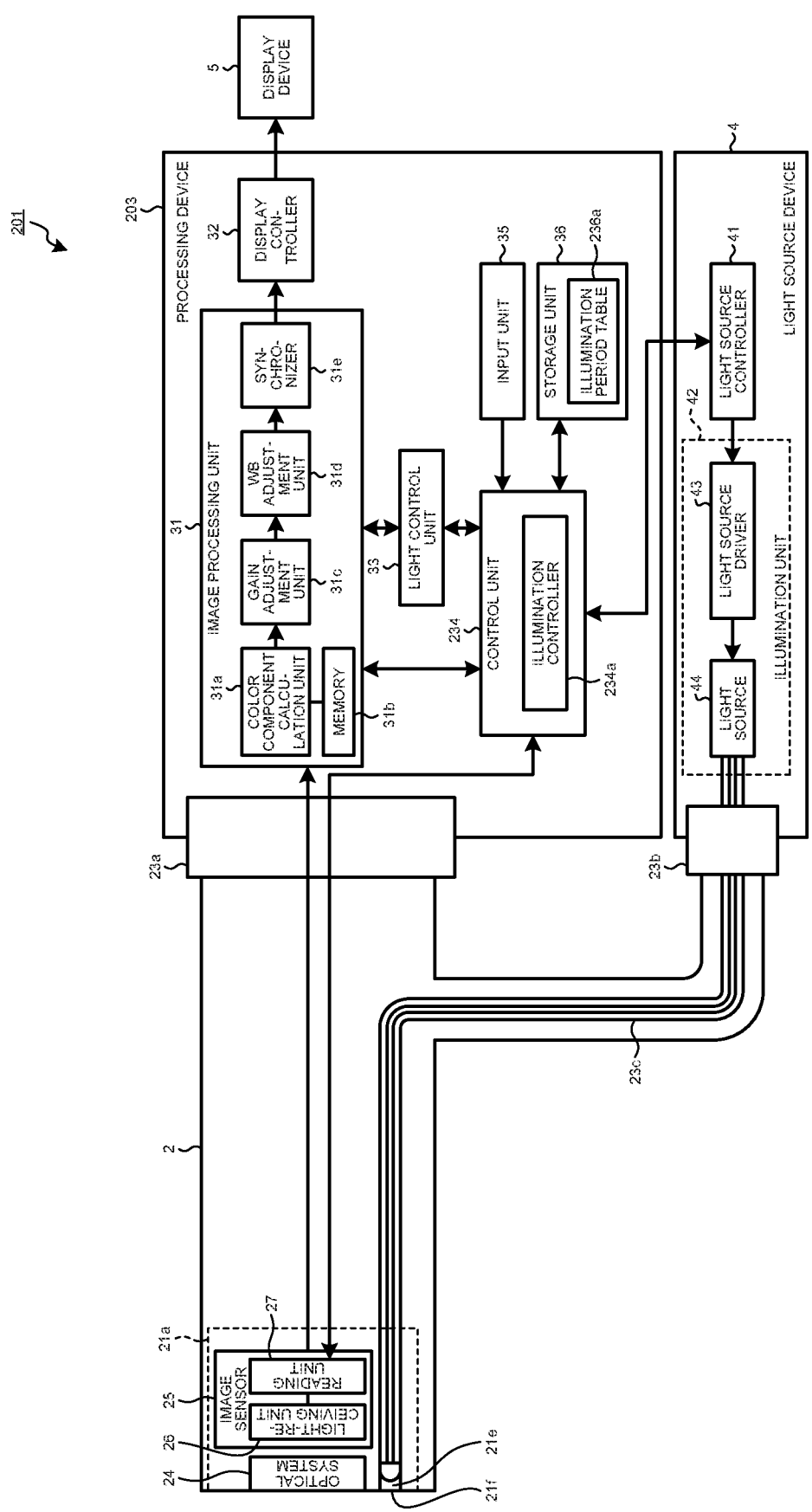
FIG. 9 is a block diagram schematically illustrating a configuration of an endoscope system according to a second embodiment.

FIG. 9 is a block diagram schematically illustrating a configuration of an endoscope system according to the second embodiment. As illustrated in FIG. 9, an endoscope system 201 according to the second embodiment includes a processing device 203 instead of the processing device 3 illustrated in FIG. 2. The processing device 203 includes a control unit 234 having an illumination controller 234a. The illumination controller 234a causes a light source device 4 to perform illumination with illumination light of two of three colors, i.e. R, G, and B, in one one-line exposure period. The illumination controller 234a causes the light source device 4 to perform an illumination process such that illumination is performed the same number of times with the illumination light of any color in three successive one-line exposure periods. The illumination controller 234a causes the light source device 4 to perform illumination in a state where illumination periods of the illumination light of two colors with which illumination is performed in the same one-line exposure period at least partially overlap.

A storage unit 36 stores an illumination period table 236a (illumination period information). The illumination period table 236a is a table which indicates a plurality of combinations of illumination periods of illumination light of respective colors with which a solution of a predetermined relational expression used by a color component calculation unit 31a is made unique. The illumination controller 234a causes the light source device 4 to perform illumination with illumination light of respective colors for illumination periods included in, among combinations of illumination periods of illumination light of respective colors indicated in the illumination period table 236a, a combination which includes illumination periods closest to illumination periods of illumination light of respective colors obtained by a light control unit 33.

Figure 10:
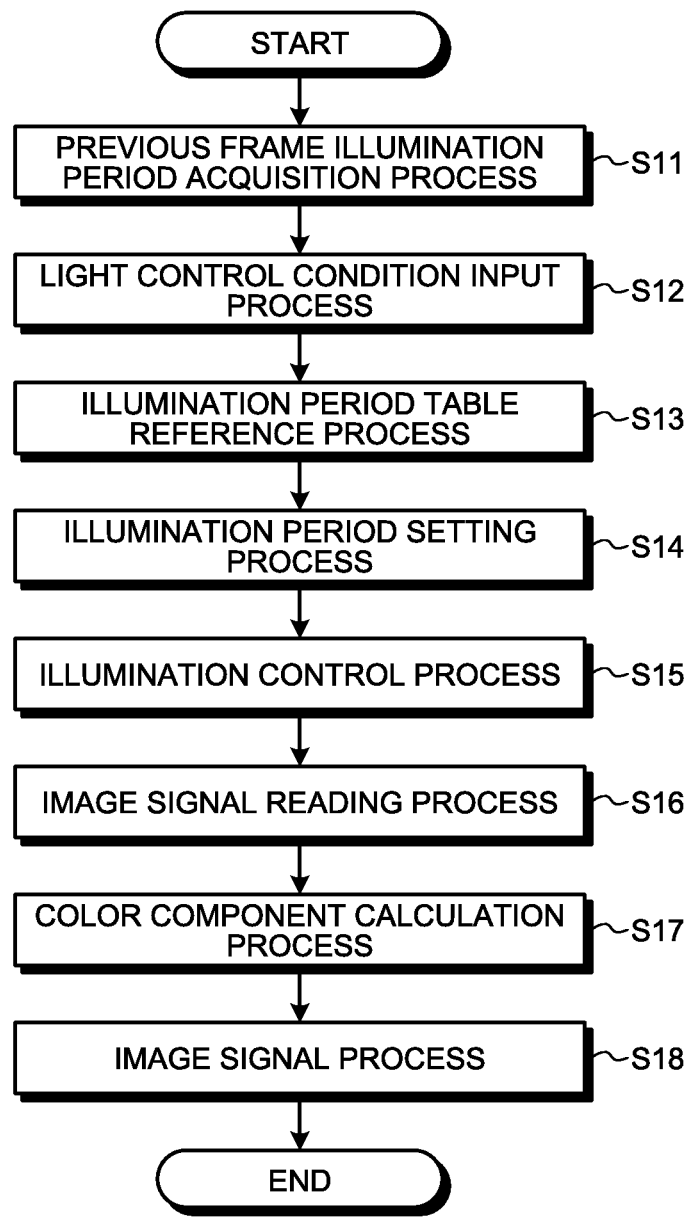
FIG. 10 is a flowchart illustrating a processing procedure of a process until an RGB image signal of one frame is generated in a processing device illustrated in FIG. 9.

FIG. 10 is a flowchart illustrating a processing procedure of a process until an RGB image signal of one frame is generated in the processing device 203. The illumination controller 234a performs a previous frame illumination period acquisition process for acquiring an illumination period of a previous frame (Step S11). In Step S11, the illumination controller 234a acquires illumination periods of two types of light in the previous frame located one frame before the latest frame. Step S12 is Step S1 illustrated in FIG. 3. The illumination controller 234a performs an illumination period table reference process for referring to the illumination period table 236a of the storage unit 36 (Step S13). The illumination controller 234a performs an illumination period setting process for setting illumination periods of respective colors to be used for next illumination for illumination periods included in, among combinations of illumination periods of illumination light of respective colors indicated in the illumination period table 236a, a combination which includes illumination periods closest to illumination periods of illumination light of respective colors obtained by the light control unit 33, in view of the illumination period of the previous frame acquired in Step S11 (Step S14). The illumination controller 234a performs an illumination control process for causing the light source device 4 to perform illumination with each illumination light for the set illumination period (Step S15). Steps S16 to S18 are Steps S3 to S5 illustrated in FIG. 3.

Figure 11:
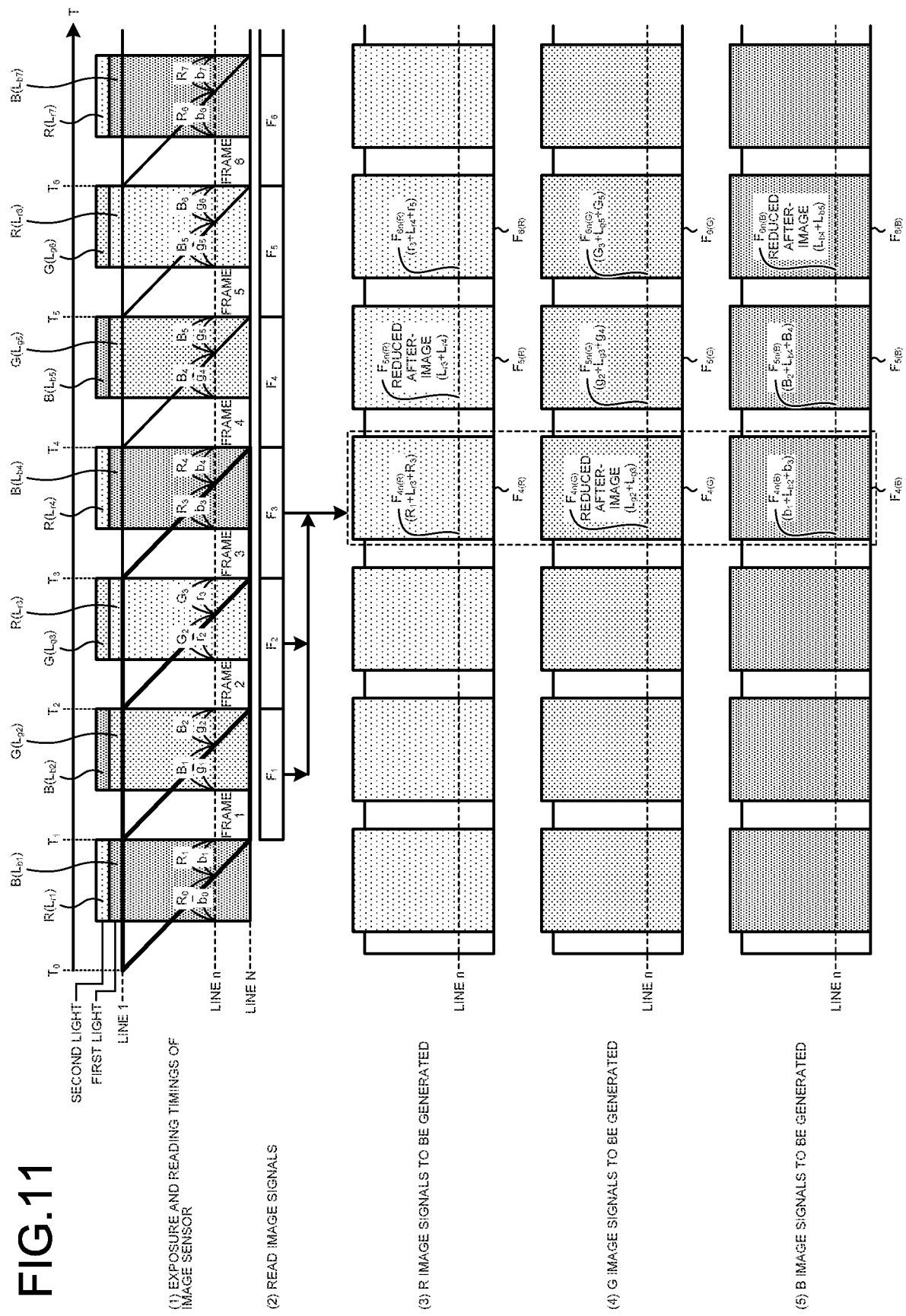
FIG. 11 is a timing chart illustrating exposure and reading timings in an image sensor illustrated in FIG. 9.

Next, some processes illustrated in FIG. 10 will be described with reference to FIG. 11. FIG. 11 is a timing chart illustrating exposure and reading timings in the image sensor 25 illustrated in FIG. 9. FIG. 11 also illustrates image signals ((2) of FIG. 11) read from the image sensor 25 in accordance with the exposure and reading timings of the image sensor 25 ((1) of FIG. 11), and R, G, and B image signals generated based on the image signals ((3) to (5) of FIG. 11). In (3) to (5) of FIG. 11, timing for generating an image signal of each color component is illustrated to be shifted from actual timing for ease of description of an image signal used for generating the image signal of each color component.

The illumination controller 234a causes the light source device 4 to execute the illumination period setting process (Step S14) for performing illumination with illumination light of two of three colors, i.e. R, G, and B, in one one-line exposure period for the illumination period set in Step S13 such that illumination is performed the same number of times with the illumination light of any color in successive three one-line exposure periods. Furthermore, the illumination controller 234a causes the light source device 4 to perform illumination in a state where illumination periods of the illumination light of two colors with which illumination is performed in the same one-line exposure period at least partially overlap. Then, similarly to the first embodiment, the illumination controller 234a causes the light source device 4 to turn off any of the light at termination time $T_1$, $T_2$, $T_3$, $T_4$, or $T_5$ of the one-line exposure period of each frame.

Specifically, in a one-line exposure period of frame 1, irradiation with B light as first light is performed for an illumination period $L_{b1}$ and illumination with R light as second light is performed for an illumination period $L_{r1}$; in a one-line exposure period of frame 2, irradiation with G light as first light is performed for an illumination period $L_{g2}$ and illumination with B light as second light is performed for an illumination period $L_{b2}$; and in a one-line exposure period of frame 3, irradiation with R light as first light is performed for an illumination period $L_{r3}$ and illumination with G light as second light is performed for an illumination period $L_{g3}$. Regarding subsequent frames, illumination is performed the same number of times with the illumination light of any color in three successive frames, and illumination is performed in a state where illumination periods of the illumination light of two colors with which illumination is performed in the same one-line exposure period at least partially overlap.

Each of output values of image signals $F_1$ to $F_5$ of frames read by the image signal reading process in Step S16 is a value corresponding to exposure of light of a plurality of colors in accordance with variations in colors and the number of illumination light, the number of illumination times, and illumination periods, depending on horizontal lines. In the second embodiment, a simultaneous linear equation with three unknowns holds (expression (1)) which indicates a relationship among values of output image signals $F_{(k-3)n}$, $F_{(k-2)n}$, and $F_{(k-1)n}$ of a horizontal line n in successive frames (k-3) to (k-1), a matrix $A_k$ based on respective illumination periods of first light and second light in each one-line exposure period in the successive frames (k-3) to (k-1) and respective exposure periods of the first light and the second light to the horizontal line n in the frames (k-3) to (k-1), and an R image signal $F_{kn(R)}$, a G image signal $F_{kn(G)}$, and a B image signal $F_{kn(B)}$ of the horizontal line n in a frame k. The color component calculation unit 31a solves, for each horizontal line n, Expression (2) to obtain an inverse matrix $A_k^{-1}$ of the matrix $A_k$ corresponding to the second embodiment, and obtains the R image signal $F_{kn(R)}$, the G image signal $F_{kn(G)}$, and the B image signal $F_{kn(B)}$ of the horizontal line n in the frame k.

In the second embodiment, parameters of the matrix $A_k$ are the illumination periods of the first light and the second light in each one-line exposure period in the successive frames (k-3) to (k-1), and respective exposure periods of the first light and the second light to the horizontal line n in the frames (k-3) to (k-1). For example, an R image signal $F_{4n(R)}$, a G image signal $F_{4n(G)}$, and a B image signal $F_{4n(B)}$ of the horizontal line n in a fourth frame are obtained by inputting, to Expression (6) below, output values of image signals $F_{1n}$, $F_{2n}$, and $F_{3n}$ of the horizontal line n in frames 1 to 3.

$$A_4 \begin{bmatrix} F_{4n(R)} \\ F_{4n(G)} \\ F_{4n(B)} \end{bmatrix} = \begin{bmatrix} F_{3n} \\ F_{2n} \\ F_{1n} \end{bmatrix} \begin{bmatrix} \frac{r_3 + R_3}{R_1 + L_{r3} + R_3} & \frac{G_3}{L_{g2} + L_{g3}} & \frac{b_3}{b_1 + L_{b2} + b_3} \\ \frac{r_2}{R_1 + L_{r3} + R_3} & \frac{g_2 + G_2}{L_{g2} + L_{g3}} & \frac{B_2}{b_1 + L_{b2} + b_3} \\ \frac{R_1}{R_1 + L_{r3} + R_3} & \frac{g_1}{L_{g2} + L_{g3}} & \frac{b_1 + B_1}{b_1 + L_{b2} + b_3} \end{bmatrix} \quad (6)$$

$$\begin{bmatrix} F_{4n(R)} \\ F_{4n(G)} \\ F_{4n(B)} \end{bmatrix} = \begin{bmatrix} F_{3n} \\ F_{2n} \\ F_{1n} \end{bmatrix}$$

In Expression (6), parameters of a matrix $A_4$ in a calculation expression in the fourth frame are respective illumination periods $L_{b1}$, $L_{g2}$, and $L_{r3}$ of the B light, the G light, and the R light as first light and respective illumination periods $L_{r1}$, $L_{b2}$, and $L_{g3}$ of the R light, the B light, and the G light as second light in successive frames 1, 2, and 3, as well as exposure periods $b_1$ and $b_3$ of the B light as the first light, exposure periods $g_1$ and $g_2$ of the G light as the first light, and exposure periods $r_2$ and $r_3$ of the R light as the first light; and exposure periods $R_1$ and $R_3$ of the R light as the second light, exposure periods $B_1$ and $B_2$ of the B light as the second light, and exposure periods $G_2$ and $G_3$ of the G light as the second light, to the horizontal line n in frames 1 to 3. Hereinafter, a row vector ($r_3+R_3$, $G_3$, $b_3$) constituted by numerator components in a first row of the matrix $A_4$ in Expression (6) is denoted by Sa, a row vector ($r_2$, $g_2+G_2$, $B_2$) constituted by numerator components in a second row thereof is denoted by Sb, and a row vector ($R_1$, $g_1$, $b_1+B_1$) constituted by numerator components in a third row thereof is denoted by Sc.

The color component calculation unit 31a performs a calculation process to solve Expression (6) to which the illumination periods and the exposure periods of each of the first color and the second color corresponding to the horizontal line n have been applied as the parameters of the matrix $A_4$, and output values of the horizontal line n of the image signals $F_{3n}$, $F_{2n}$, and $F_{1n}$ have been input. As a result, the color component calculation unit 31a can generate the R image signal $F_{4n(R)}$ corresponding to an image signal in a case where exposure has been performed with the R light for a period ($R_1+L_{r3}+R_3$), the G image signal $F_{4n(G)}$ corresponding to an image signal in a case where exposure has been performed with the G light for a period ($L_{g2}+L_{g3}$), and the B image signal $F_{4n(B)}$ corresponding to an image signal in a case where exposure has been performed with the B light for a period ($b_1+L_{b2}+b_3$), each of which corresponding to the horizontal line n in the fourth frame. The color component calculation unit 31a sequentially performs calculation processes to solve Expression (6) in which parameters corresponding to each horizontal line n are used as parameters of the matrix $A_k$, and to which output values of the image signals $F_{3n}$, $F_{2n}$, and $F_{1n}$ of the horizontal line n to be calculated have been input, from a top horizontal line 1 to a last horizontal line N, respectively. As a result, the color component calculation unit 31a can acquire an R image signal $F_{4(R)}$, a G image signal $F_{4(G)}$, and a B image signal $F_{4(B)}$ of the fourth frame on a per frame basis. Regarding a fifth frame, similarly, by applying corresponding parameters to the matrix $A_k$ of Expression (6), and calculating an inverse matrix $A_k^{-1}$ of the matrix $A_k$ for each horizontal line n to generate image signals of respective color components (an R image signal $F_{5n(R)}$, a G image signal $F_{5n(G)}$, and a B image signal $F_{5n(B)}$) for each horizontal line n, an R image signal $F_{5(R)}$, a G image signal $F_{5(G)}$, and a B image signal $F_{5(B)}$ of the fifth frame are acquired on a per frame basis. The same holds for a sixth frame.

Next, a rank of the matrix $A_4$ in Expression (6) will be described. The matrix $A_4$ of Expression (6) can be decomposed as indicated by the following Expression (7).

$$A_4 = (A_{4-1} + A_{4-2})A_{4-3} = \left( \begin{bmatrix} r_3 & 0 & b_3 \\ r_2 & g_2 & 0 \\ 0 & g_1 & b_1 \end{bmatrix} + \begin{bmatrix} R_3 & G_3 & 0 \\ 0 & G_2 & B_2 \\ R_1 & 0 & B_1 \end{bmatrix} \right) \quad (7)$$

$$\begin{bmatrix} \frac{1}{R_1 + L_{r3} + R_3} & 0 & 0 \\ 0 & \frac{1}{L_{g2} + L_{g3}} & 0 \\ 0 & 0 & \frac{1}{b_1 + L_{b2} + b_3} \end{bmatrix}$$

As indicated by Expression (7), the matrix $A_4$ can be decomposed into a matrix $A_{4-1}$ in which each of the exposure time $r_2$, $r_3$, $g_1$, $g_2$, $b_1$, and $b_3$ by the first light is a parameter, a matrix $A_{4-2}$ in which each of the exposure time $R_1$, $R_3$, $G_2$, $G_3$, $B_1$, and $B_2$ by the second light is a parameter, and a matrix $A_{4-3}$ in which a reciprocal of a sum of the irradiation period of the first light and the irradiation period of the second light is a parameter. Among them, the matrix $A_{4-3}$ is a diagonal matrix. Therefore, a rank thereof is 3, and there exists an inverse matrix thereof. Therefore, when a rank of a matrix obtained by adding the matrix $A_{4-1}$ and the matrix $A_{4-2}$ is 3, the solution of Expression (6) is unique. Hereinafter, a row vector ($r_3$, 0, $b_3$) constituted by components in a first row of the matrix $A_{41}$ in Expression (7) is denoted by Saa, a row vector ($r_2$, $g_2$, 0) constituted by components in a second row thereof is denoted by Sba, and a row vector (0, $g_1$, $b_1$) constituted by components in a third row thereof is denoted by Sca. A row vector ($R_3$, $G_3$, 0) constituted by components in a first row of the matrix $A_{4-2}$ in Expression (7) is denoted by Sab, a row vector (0, $G_2$, $B_2$) constituted by components in a second row thereof is denoted by Sbb, and a row vector ($R_1$, 0, $B_1$) constituted by components in a third row thereof is denoted by Scb.

Figure 12:
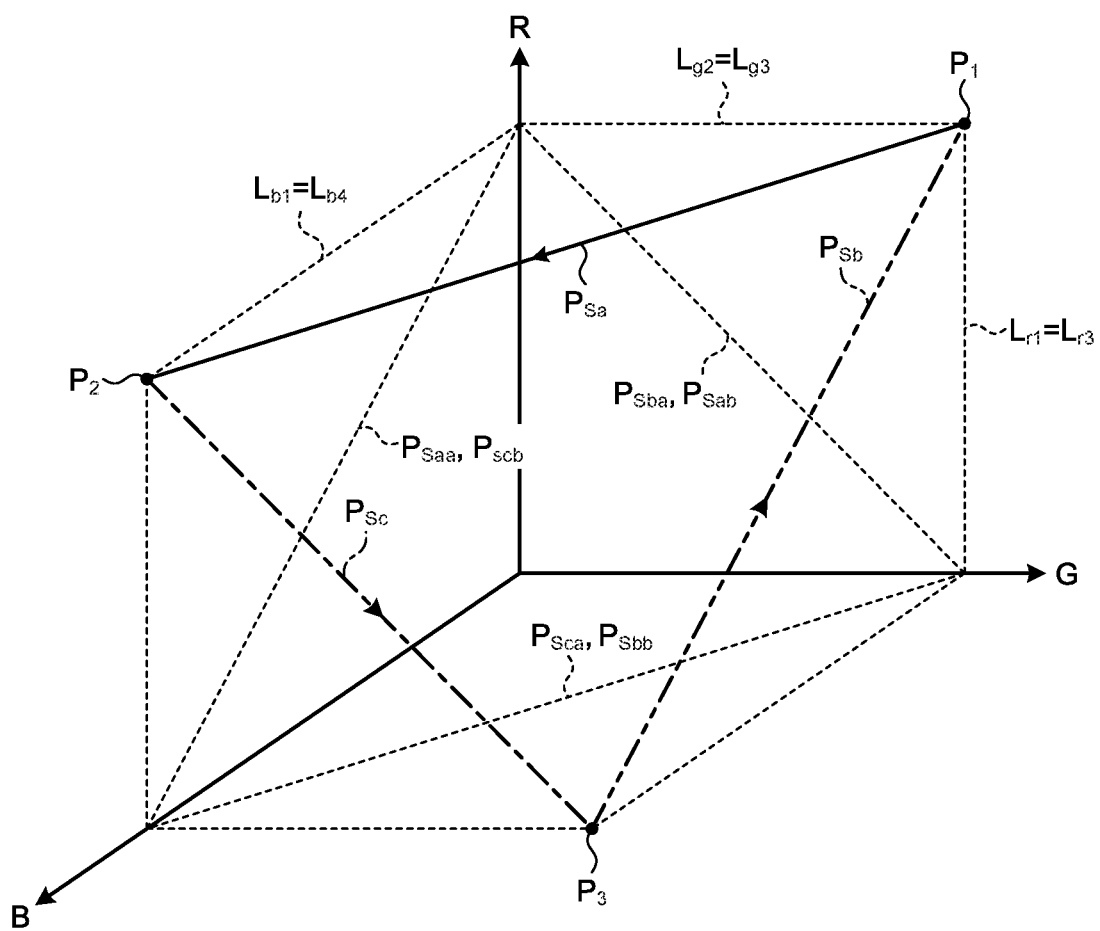
FIG. 12 is a diagram explaining uniqueness of a solution of image signals obtained in the second embodiment.

FIG. 12 is a diagram explaining uniqueness of a solution of image signals obtained in the second embodiment, and illustrating a case where the row vectors Saa, Sba, and Sca of the matrix $A_{4-1}$ and the row vectors Sab, Sbb, and Scb of the matrix $A_{4-2}$ are viewed in an RGB space. FIG. 12 illustrates a case in where illumination periods are all the same period for any colors and light control is not performed. In that case, the row vectors Saa and Scb respectively depict same loci $P_{Saa}$ and $P_{Scb}$ on an R-B plane. The row vectors Sba and Sab respectively depict same loci $P_{Sba}$ and $P_{Sab}$ on an R-G plane, and the row vectors Sca and Sbb respectively depict same loci $P_{Sca}$ and $P_{Sbb}$ on a G-B plane. Therefore, eventually, the row vector Sa in Expression (6) follows a locus $P_{Sa}$ including a point $P_1$ as an origin point and a point $P_2$ as an end point, the row vector Sb follows a locus $P_{Sb}$ including a point $P_3$ as an origin point and the point $P_1$ as an end point, and the row vector Sc follows a locus $P_{Sc}$ including the point $P_2$ as an origin point and the point $P_3$ as an end point. Consequently, the row vectors Sa to Sc are always linearly independent and the rank of the matrix $A_4$ is 3. Therefore, there exists an inverse matrix $A_4^{-1}$ of the matrix $A_4$ in Expression (6), and the solution of Expression (6) is unique.

Figure 13:
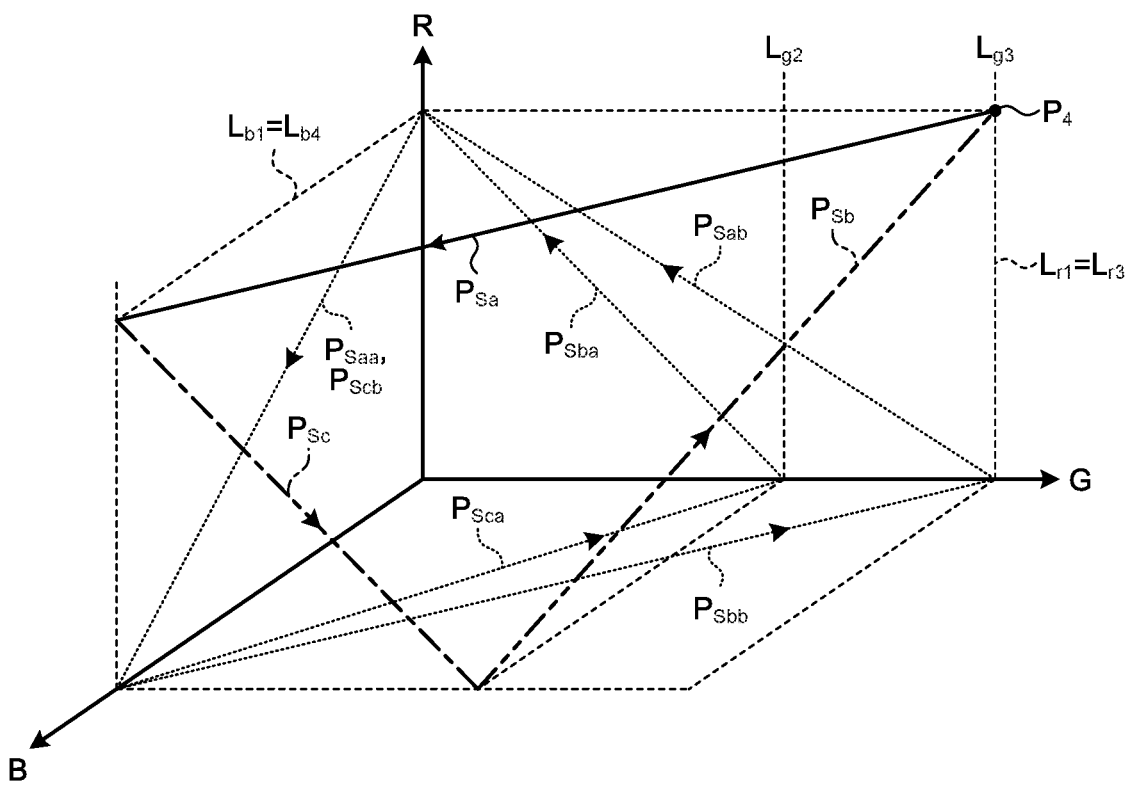
FIG. 13 is a diagram explaining uniqueness of a solution of image signals obtained in the second embodiment.

FIG. 13 is a diagram explaining uniqueness of a solution of image signals obtained in the second embodiment, and illustrating another example of the case where the row vectors Saa, Sba, and Sca of the matrix $A_{4-1}$ and the row vectors Sab, Sbb, and Scb of the matrix $A_{4-2}$ are viewed in the RGB space. In FIG. 13, a case will be described in which among the illumination periods of respective colors, the illumination periods of respective colors other than the illumination period $L_{g3}$ of the G light as the second light of frame 3 are all the same period, and light control is performed such that only the illumination period $L_{g3}$ is longer than other illumination periods.

In that case, although the row vectors Sba and Sab respectively depict different loci $P_{Sba}$ and $P_{Sab}$ on the R-B plane, end points thereof coincide with each other. In addition, although the row vectors Sca and Sbb respectively depict different loci $P_{Sca}$ and $P_{Sbb}$ on the G-B plane, origin points thereof coincide with each other. Consequently, as compared to the case of FIG. 12, an only difference therefrom resides in that the origin point of the locus $P_{sa}$ of the row vector Sa and the end point of the locus $P_{sb}$ of the row vector Sb in Expression (6) are at a point $P_4$ corresponding to the illumination period $L_{g3}$, eventually, and the row vectors Sa to Sc are always linearly independent and the rank of the matrix $A_4$ is 3. Therefore, there exists an inverse matrix $A_4^{-1}$ of the matrix $A_4$ in Expression (6) even when the light control is performed, and the solution of Expression (6) is unique. Consequently, since the solution of Expression (6) is unexceptionally unique irrespective of whether light control is performed for R, G, and B, a value of each of the R image signal $F_{4n(R)}$, the G image signal $F_{4n(G)}$, and the B image signal $F_{4n(B)}$ can be obtained through calculation. In the second embodiment, calculation by the color component calculation unit 31a is simplified by performing illumination with respective types of light using a combination of illumination periods closest to a light control condition among combinations of illumination periods of illumination light of respective colors, with which combinations a solution of a relational expression (Expression (6)) used by the color component calculation unit 31a is made unique.

In the above color component calculation process (Step S17), all of the R, G, and B image signals are calculated in one frame. In an image signal process (Step S18), a synchronizer 31e adopts in a synchronization process, among the R, G, and B image signals, an image signal of a color used for exposure in two periods close to a reading period of the last frame of the three successive frames used for the calculation, since the image signal provides a reduced afterimage. For example, in the fourth frame, the G image signal $F_{4(G)}$ corresponding to two periods of the exposure period $L_{g3}$ close to the reading period $T_3$ to $T_4$ in frame 3 and the exposure period $L_{g2}$ is adopted; in the fifth frame, the R image signal $F_{5(R)}$ corresponding to two periods of the exposure period $L_{r4}$ closest to the reading period $T_4$ to $T_5$ in frame 4 and the exposure period $L_{r3}$ is adopted; and in the sixth frame, the B image signal $F_{6(B)}$ corresponding to the exposure period $L_{b5}$ closest to the reading period $T_5$ to $T_6$ in frame 5 and the exposure period $L_{b4}$ is adopted. The synchronization process is performed using the adopted R image signal $F_{4(R)}$, G image signal $F_{5(G)}$, and B image signal $F_{6(B)}$ to generate an RGB image signal.

A similar effect to that of the first embodiment is obtained even in a case where light emission is performed with two colors of light in one frame, as in the second embodiment, since an image signal of each color component of a frame to be acquired is extracted in a calculation process using output values of image signals of a plurality of successive frames. Furthermore, in the second embodiment, it is possible to reduce an afterimage occurring when an object moves since illumination frequency of each color increases as compared to the first embodiment.

Figure 14:
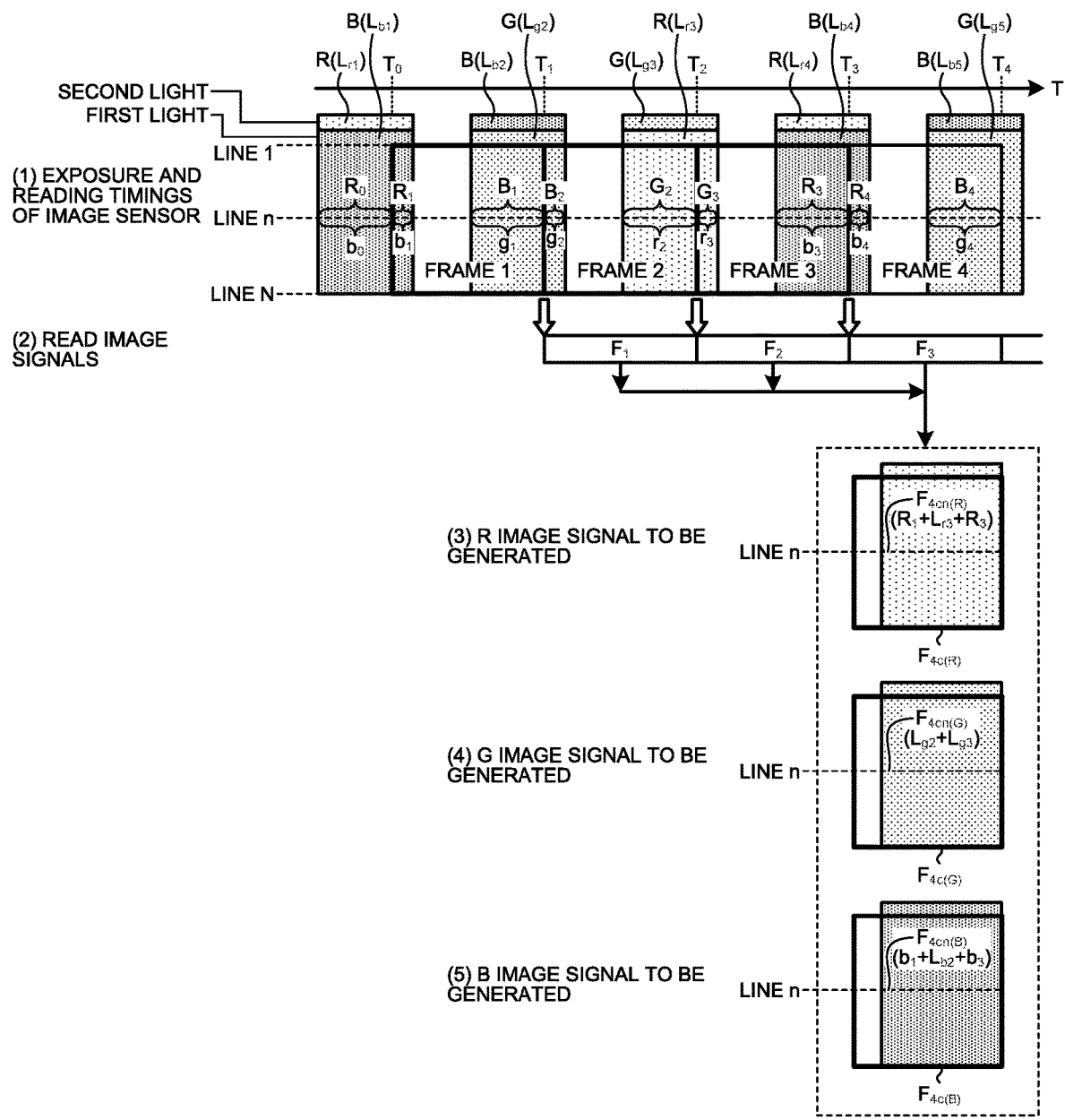
FIG. 14 is a timing chart illustrating exposure and reading timings in a case where the image sensor in the second embodiment is a CCD image sensor.

Similarly to the first embodiment, the second embodiment can be applied also to a case where the image sensor 25 is a CCD image sensor which adopts the global shutter method. FIG. 14 is a timing chart illustrating exposure and reading timings in a case where the image sensor 25 is a CCD image sensor. In a case where the illumination controller 234a causes the light source device 4 to perform irradiation with the G light, the B light, and the R light on a condition illustrated in (1) of FIG. 14 to generate, for example, an R image signal $F_{4c(R)}$, a G image signal $F_{4c(G)}$, and a B image signal $F_{4c(B)}$ of the fourth frame, output values of the three successive frame image signals $F_1$ to $F_3$ (see (2) of FIG. 14) are input to Expression (6) for each horizontal line to perform calculation. Also in that case, as with the case of a CMOS image sensor, parameters of the matrix $A_4$ of Expression (6) are respective illumination periods $L_{b1}$, $L_{g2}$, and $L_{r3}$ of the B light, the G light, and the R light as first light and respective illumination periods $L_{r1}$, $L_{b2}$, and $L_{g3}$ of the R light, the B light, and the G light as second light in successive frames 1 to 3 regarding the horizontal line n, as well as exposure periods $b_1$ and $b_3$ of the B light as the first light, exposure periods $g_1$ and $g_2$ of the G light as the first light, and exposure periods $r_2$ and $r_3$ of the R light as the first light; and exposure periods $R_1$ and $R_3$ of the R light as the second light, exposure periods $B_1$ and $B_2$ of the B light as the second light, and exposure periods $G_2$ and $G_3$ of the G light as the second light, to the horizontal line n in frames 1 to 3.

Similarly to the first embodiment, the second embodiment can be applied also to the NBI observation method. In that case, the illumination controller 234a may cause an illumination process to be executed such that illumination is performed the same number of times with the illumination light of any color in three successive frame periods. In the illumination process, illumination is performed with illumination light of two of three colors in one one-line exposure period on a similar condition to that of irradiation with the R light, the G light, and the B light using any of patterns of a combination of the V light, the G light, and no light, a combination of the V light, the G light, and VV light, or a combination of the V light, the G light, and GG light (second G light). In the second embodiment, the description has been given using, as an example, the case in which illumination is performed in a state where illumination periods of the illumination light of two colors with which illumination is performed in the same one-line exposure period at least partially overlap. However, when the condition is satisfied with which a rank of the matrix $A_k$ is 3, there is no need for the illumination periods of the illumination light of two colors with which illumination is performed in the same one-line exposure period to overlap.

Third Embodiment

Next, a third embodiment will be described. In the third embodiment, a case will be described in which illumination is performed with illumination light of all three colors in one one-line exposure period.

Figure 15:
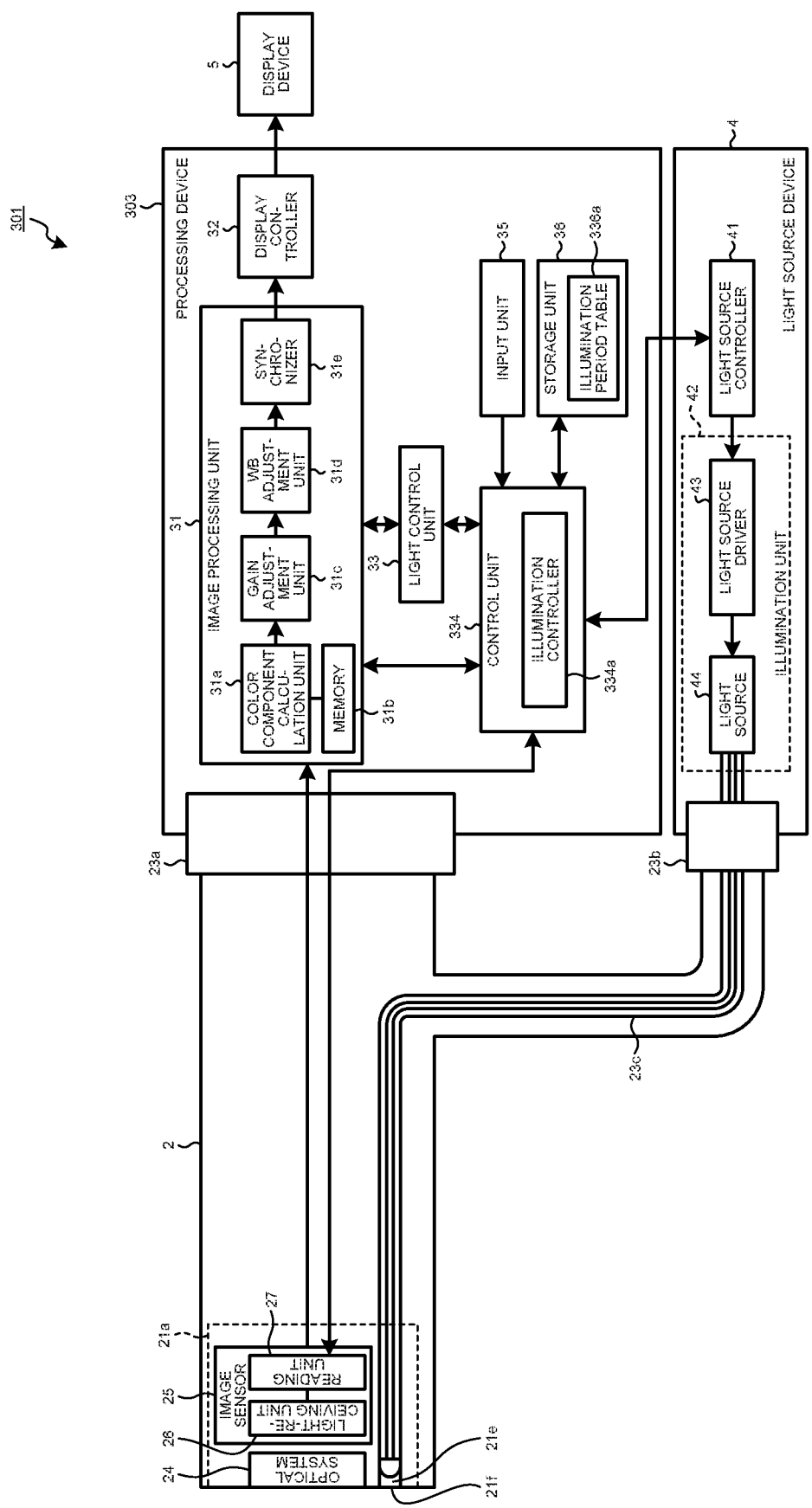
FIG. 15 is a block diagram schematically illustrating a configuration of an endoscope system according to a third embodiment.

FIG. 15 is a block diagram schematically illustrating a configuration of an endoscope system according to the third embodiment. As illustrated in FIG. 15, an endoscope system 301 according to the third embodiment includes a processing device 303 instead of the processing device 203 illustrated in FIG. 9. The processing device 303 includes a control unit 334 having an illumination controller 334a. The illumination controller 334a causes a light source device 4 to perform illumination with illumination light of all three colors, i.e. R, G, and B, in one one-line exposure period, for different illumination periods, respectively. The illumination controller 334a causes the light source device 4 to perform illumination with illumination light of three colors so as to include a period during which the illumination light of all three colors, with which illumination is performed in the same one-line exposure period, is used for illumination in an overlapping manner.

Similarly to the second embodiment, a storage unit 36 stores an illumination period table 336a (illumination period information) which indicates a plurality of combinations of illumination periods of illumination light of respective colors with which a solution of a predetermined relational expression used by a color component calculation unit 31a is made unique. The illumination controller 334a causes the light source device 4 to perform illumination with illumination light of respective colors for illumination periods included in, among combinations of illumination periods of illumination light of respective colors indicated in the illumination period table 336a, a combination which includes illumination periods closest to illumination periods of illumination light of respective colors obtained by a light control unit 33.

Figure 16:
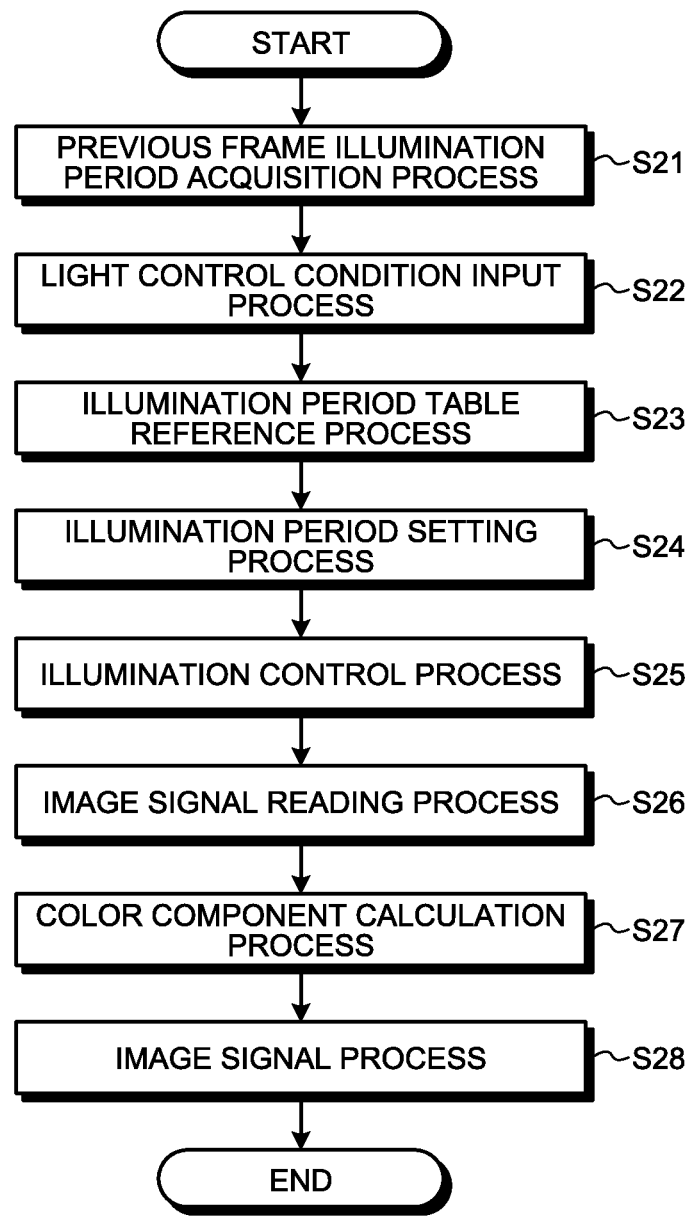
FIG. 16 is a flowchart illustrating a processing procedure of a process until an RGB image signal of one frame is generated in a processing device illustrated in FIG. 15.

FIG. 16 is a flowchart illustrating a processing procedure of a process until an RGB image signal of one frame is generated in the processing device 303. The illumination controller 334a performs a previous frame illumination period acquisition process for acquiring illumination periods of previous frames (Step S21). In Step S21, the illumination controller 334a acquires illumination periods of three types of light in a frame located one frame before the latest frame and illumination periods of three types of light in a frame located two frames before the latest frame. Step S22 is Step S1 illustrated in FIG. 3. The illumination controller 334a performs an illumination period table reference process for referring to the illumination period table 336a of the storage unit 36 (Step S23). The illumination controller 334a performs an illumination period setting process for setting illumination periods of respective colors to be used for next illumination for illumination periods included in, among combinations of illumination periods of illumination light of respective colors indicated in the illumination period table 336a, a combination which includes illumination periods closest to illumination periods of illumination light of respective colors obtained by the light control unit 33, in view of the illumination periods of the previous frames acquired in Step S21 (Step S24). The illumination controller 334a performs an illumination control process for causing the light source device 4 to perform illumination with each illumination light for the set illumination period (Step S25). Steps S26 to S28 are Steps S3 to S5 illustrated in FIG. 3.

Figure 17:
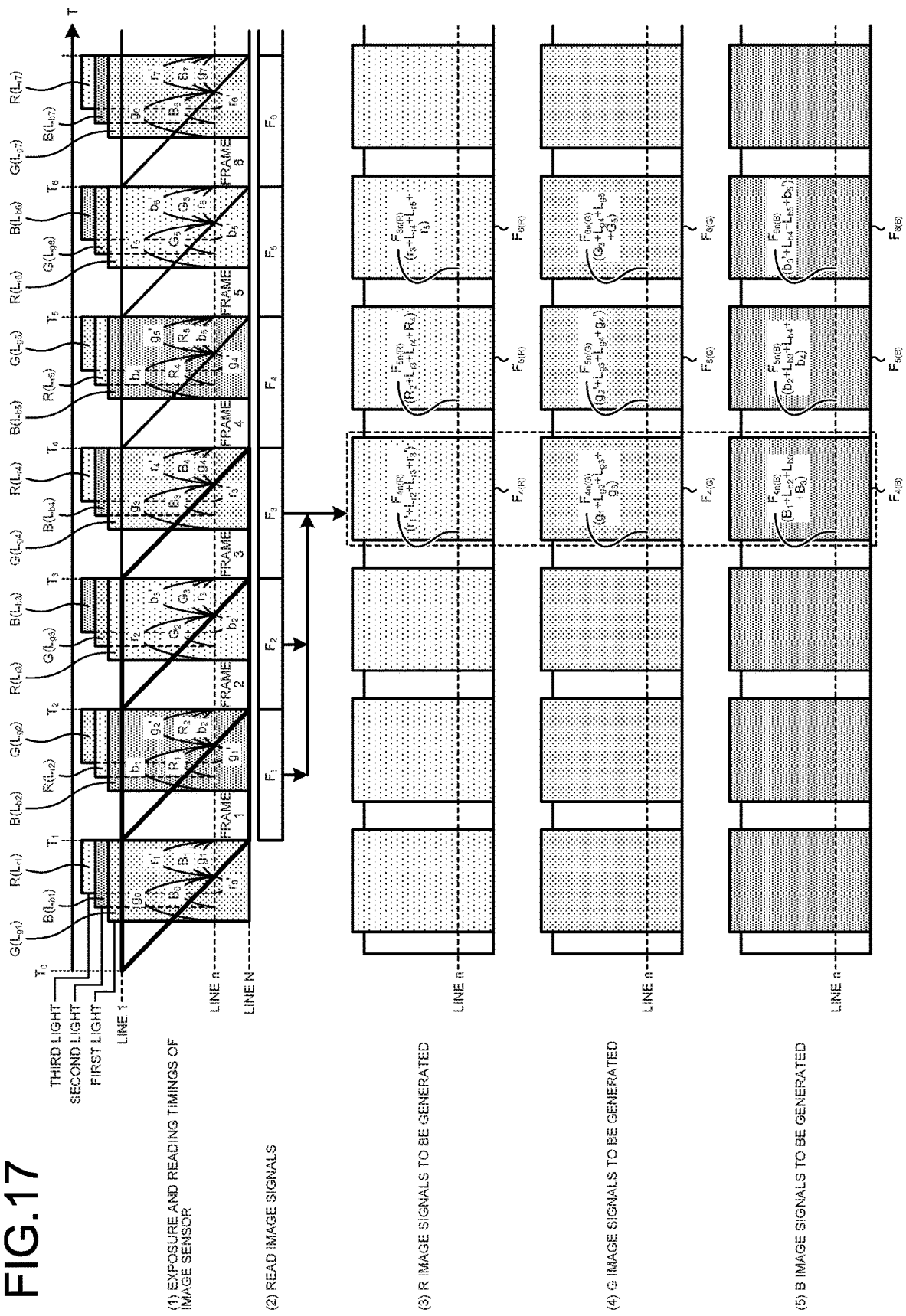
FIG. 17 is a timing chart illustrating exposure and reading timings in an image sensor illustrated in FIG. 15.

Next, some processes illustrated in FIG. 16 will be described with reference to FIG. 17. FIG. 17 is a timing chart illustrating exposure and reading timings in the image sensor 25 illustrated in FIG. 15. FIG. 17 also illustrates image signals ((2) of FIG. 17) read from the image sensor 25 in accordance with exposure and reading timings of the image sensor 25 ((1) of FIG. 17), and R, G, and B image signals generated based on the image signals ((3) to (5) of FIG. 17). In (3) to (5) of FIG. 17, timing for generating an image signal of each color component is illustrated to be shifted from actual timing for ease of description of an image signal used for generating the image signal of each color component.

The illumination controller 334a causes the light source device 4 to execute the illumination process (Step S24) for performing illumination with illumination light of all three colors of R, G, and B in one one-line exposure period for the illumination period set in Step S23 such that illumination is performed for illumination periods which are different periods for each of the three colors in the same one-line exposure period. Furthermore, the illumination controller 334a causes the light source device 4 to perform illumination with illumination light of three colors so as to include a period during which the illumination light of all three colors, with which illumination is performed in the same one-line exposure period, is used for illumination in an overlapping manner. Then, similarly to the first embodiment, the illumination controller 334a causes the light source device 4 to turn off any of the light at termination time $T_1$, $T_2$, $T_3$, $T_4$, or $T_5$ of the one-line exposure period of each frame.

Specifically, in the one-line exposure period of frame 1, irradiation with the G light as first light is performed for an illumination period $L_{g1}$, illumination with the B light as second light is performed for an illumination period $L_{b1}$ ($<L_{g1}$), and illumination with the R light as third light is performed for an illumination period $L_{r1}$ ($<L_{b1}$). In the one-line exposure period of frame 2, irradiation with the B light as first light is performed for an illumination period $L_{b2}$, illumination with the R light as second light is performed for an illumination period $L_{r2}$ ($<L_{b2}$), and illumination with the G light as third light is performed for an illumination period $L_{g2}$ ($<L_{r2}$). In the one-line exposure period of frame 3, irradiation with the R light as first light is performed for an illumination period $L_{r3}$, illumination with the G light as second light is performed for an illumination period $L_{g3}$ ($<L_{r3}$), and illumination with the B light as third light is performed for an illumination period $L_{b3}$ ($<L_{g3}$). Regarding subsequent frames, illumination with illumination light of three colors is performed such that illumination is performed for illumination periods which are different periods for each of the three colors in the same one-line exposure period, and that a period is included during which the illumination light of all three colors, with which illumination is performed in the same one-line exposure period, is used for illumination in an overlapping manner.

Each of output values of image signals $F_1$ to $F_5$ of frames read by an image signal reading process in Step S26 is a value corresponding to exposure of light of a plurality of colors in accordance with variations in colors and the number of illumination light, the number of illumination times, and illumination periods, depending on horizontal lines. In the third embodiment, a simultaneous linear equation with three unknowns (expression (1)) holds which indicates a relationship among values of output image signals $F_{(k-3)n}$, $F_{(k-2)n}$, and $F_{(k-1)n}$ of a horizontal line n in successive frames (k-3) to (k-1), a matrix $A_k$ based on respective illumination periods of first light, second light, and third light in each one-line exposure period in the successive frames (k-3) to (k-1) and respective exposure periods of the first light, the second light, and the third light to the horizontal line n in the frames (k−3) to (k-1), and an R image signal $F_{kn(R)}$, a G image signal $F_{kn(G)}$, and a B image signal $F_{kn(B)}$ of the horizontal line n in a frame k. The color component calculation unit 31a solves, for each horizontal line, Expression (2) to obtain an inverse matrix $A_k^{-1}$ of the matrix $A_k$ corresponding to the third embodiment, and obtains the R image signal $F_{kn(R)}$, the G image signal $F_{kn(G)}$, and the B image signal $F_{kn(B)}$ of the horizontal line n in the frame k.

In the third embodiment, parameters of the matrix $A_k$ are the illumination periods of the first light, the second light, and the third light in each one-line exposure period in the successive frames (k-3) to (k-1), and respective exposure periods of the first light, the second light, and the third light to the horizontal line n in the frames (k-3) to (k-1). For example, an R image signal $F_{4n(R)}$, a G image signal $F_{4n(G)}$, and a B image signal $F_{4n(B)}$ of the horizontal line n in a fourth frame are obtained by inputting, to Expression (8) below, output values of the horizontal line n in image signals $F_{1n}$, $F_{2n}$, and $F_{3n}$ of frames 1 to 3.

$$A_4 \begin{bmatrix} F_{4n(R)} \\ F_{4n(G)} \\ F_{4n(B)} \end{bmatrix} = \begin{bmatrix} F_{3n} \\ F_{2n} \\ F_{1n} \end{bmatrix} \quad (8)$$

$$\begin{bmatrix} \dfrac{r_3 + r_3'}{r_1' + L_{r2} + L_{r3} + r_3'} & \dfrac{g_3 + G_3}{g_1 + L_{g2} + L_{g3} + g_3} & \dfrac{B_3 + b_3'}{B_1 + L_{b2} + L_{b3} + B_3} \\ \dfrac{r_2 + R_2}{r_1' + L_{r2} + L_{r3} + r_3'} & \dfrac{G_2 + g_2'}{g_1 + L_{g2} + L_{g3} + g_3} & \dfrac{b_2 + b_2'}{B_1 + L_{b2} + L_{b3} + B_3} \\ \dfrac{R_1 + r_1'}{r_1' + L_{r2} + L_{r3} + r_3'} & \dfrac{g_1 + g_1'}{g_1 + L_{g2} + L_{g3} + g_3} & \dfrac{b_1 + B_1}{B_1 + L_{b2} + L_{b3} + B_3} \end{bmatrix}$$

$$\begin{bmatrix} F_{4n(R)} \\ F_{4n(G)} \\ F_{4n(B)} \end{bmatrix} = \begin{bmatrix} F_{3n} \\ F_{2n} \\ F_{1n} \end{bmatrix}$$

In Expression (8), parameters of a matrix $A_4$ in a calculation expression in the fourth frame are respective illumination periods $L_{g1}$, $L_{b2}$, and $L_{r3}$ of the G light, the B light, and the R light as first light, respective illumination periods $L_{b1}$, $L_{r2}$, and $L_{g3}$ of the B light, the R light, and the G light as second light, and respective illumination periods $L_{r1}$, $L_{g2}$, and $L_{b3}$ of the R light, the G light, and the B light as third light in successive frames 1, 2, and 3, as well as exposure periods $g_1$ and $g_3$ of the G light as the first light, exposure periods $b_1$ and $b_2$ of the B light as the first light, and exposure periods $r_2$ and $r_3$ of the R light as the first light; exposure periods $B_1$ and $B_3$ of the B light as the second light, exposure periods $R_1$ and $R_2$ of the R light as the second light, and exposure periods $G_2$ and $G_3$ of the G light as the second light; and exposure periods $r_1'$ and $r_3'$ of the R light as the third light, exposure periods $g_1'$ and $g_2'$ of the G light as the third light, and exposure periods $b_2'$ and $b_3'$ of the B light as the third light, to the horizontal line n in frames 1 to 3. Hereinafter, a row vector $(r_3+r_3', g_2+G_3, B_3+b_3')$ constituted by numerator components in a first row of the matrix $A_4$ in Expression (8) is denoted by Qa, a row vector $(r_2+R_2, G_2+g_2', b_2+b_2')$ constituted by numerator components in a second row thereof is denoted by Qb, and a row vector $(R_1+r_1', g_1+g_1', b_1+B_1)$ constituted by numerator components in a third row thereof is denoted by Qc.

The color component calculation unit 31a performs a calculation process to solve Expression (8) to which the illumination periods and the exposure time of each of the first color, the second color, and the third color corresponding to the horizontal line n have been applied as the parameters of the matrix $A_4$, and output values of the horizontal line n of the image signals $F_{3n}$, $F_{2n}$, and $F_{1n}$ have been input. As a result, it is possible to generate the R image signal $F_{4n(R)}$ corresponding to an image signal in a case where exposure has been performed with the R light for a period $(r_1'+L_{r2}+L_{r3}+r_3')$, the G image signal $F_{4n(G)}$ corresponding to an image signal in a case where exposure has been performed with the G light for a period $(g_1+L_{g2}+L_{g3}+g_3)$, and the B image signal $F_{4n(B)}$ corresponding to an image signal in a case where exposure has been performed with the B light for a period $(B_1+L_{b2}+L_{b3}+B_3)$, each of which corresponding to the horizontal line n in the fourth frame. The color component calculation unit 31a sequentially performs calculation processes to solve Expression (8) in which parameters corresponding to each horizontal line are used as parameters of the matrix $A_k$, and to which output values of the image signals $F_{3n}$, $F_{2n}$, and $F_{1n}$ of the horizontal line to be calculated have been input, from a top horizontal line 1 to a last horizontal line N, respectively. As a result, the color component calculation unit 31a can acquire an R image signal $F_{4(R)}$, a G image signal $F_{4(G)}$, and a B image signal $F_{4(B)}$ of the fourth frame on a per frame basis. Regarding a fifth frame and subsequent frames, by applying corresponding parameters to the matrix $A_k$ of Expression (8), and calculating the inverse matrix $A_k^{-1}$ of the matrix $A_k$ for each horizontal line n, the image signal of each color component is acquired for each horizontal line n.

Next, a rank of the matrix $A_4$ in Expression (8) will be described. The matrix $A_4$ of Expression (8) can be decomposed as indicated by the following Expression (9).

$$A_4 = (A_{4\text{-}11} + A_{4\text{-}12} + A_{4\text{-}13})A_{4\text{-}14} = \quad (9)$$

$$\left( \begin{bmatrix} r_3 & g_3 & 0 \\ r_2 & 0 & b_2 \\ 0 & g_1 & b_1 \end{bmatrix} + \begin{bmatrix} 0 & G_3 & B_3 \\ R_2 & G_2 & 0 \\ R_1 & 0 & B_1 \end{bmatrix} + \begin{bmatrix} r_3' & 0 & b_3' \\ 0 & g_2' & b_2' \\ r_1' & g_1' & 0 \end{bmatrix} \right)$$

$$\begin{bmatrix} \dfrac{1}{r_1' + L_{r2} + L_{r3} + r_3'} & 0 & 0 \\ 0 & \dfrac{1}{g_1 + L_{g2} + L_{g3} + g_3} & 0 \\ 0 & 0 & \dfrac{1}{B_1 + L_{b2} + L_{b3} + B_3} \end{bmatrix}$$

As indicated by Expression (9), the matrix $A_4$ can be decomposed into a matrix $A_{4\text{-}11}$ in which each of the exposure time $r_2$, $r_3$, $g_1$, $g_3$, $b_1$, and $b_2$ by the first light is a parameter, a matrix $A_{4\text{-}12}$ in which each of the exposure time $R_1$, $R_2$, $G_2$, $G_3$, $B_1$, and $B_3$ by the second light is a parameter, a matrix $A_{4\text{-}13}$ in which each of the exposure time $r_1'$, $r_3'$, $g_1'$, $g_2'$, $b_2'$, and $b_3'$ by the third light is a parameter, and a matrix $A_{4\text{-}14}$ in which a reciprocal of a sum of the irradiation period of the first light, the irradiation period of the second light, and the irradiation period of the third light is a parameter. Among them, the matrix $A_{4\text{-}14}$ is a diagonal matrix. Therefore, a rank thereof is 3, and there exists an inverse matrix thereof. Therefore, when a rank of a matrix obtained by adding the matrices $A_{4\text{-}11}$ to $A_{4\text{-}13}$ is 3, the solution of Expression (8) is unique. Hereinafter, a row vector $(r_3, g_3, 0)$ constituted by components in a first row of the matrix $A_{4\text{-}11}$ in Expression (9) is denoted by Qaa, a row vector $(r_2, 0, b_2)$ constituted by components in a second row thereof is denoted by Qba, and a row vector $(0, g_1, b_1)$ constituted by components in a third row thereof is denoted by Qca. A row vector $(0, G_3, B_3)$ constituted by components in a first row of the matrix $A_{4-12}$ in Expression (9) is denoted by Qab, a row vector $(R_2, G_2, 0)$ constituted by components in a second row thereof is denoted by Qbb, and a row vector $(R_1, 0, B_1)$ constituted by components in a third row thereof is denoted by Qcb. A row vector $(r_3', 0, b_3')$ constituted by components in a first row of the matrix $A_{4-13}$ in Expression (9) is denoted by Qac, a row vector $(0, g_2', b_2')$ constituted by components in a second row thereof is denoted by Qbc, and a row vector $(r_1', g_1', 0)$ constituted by components in a third row thereof is denoted by Qcc.

Figure 18:
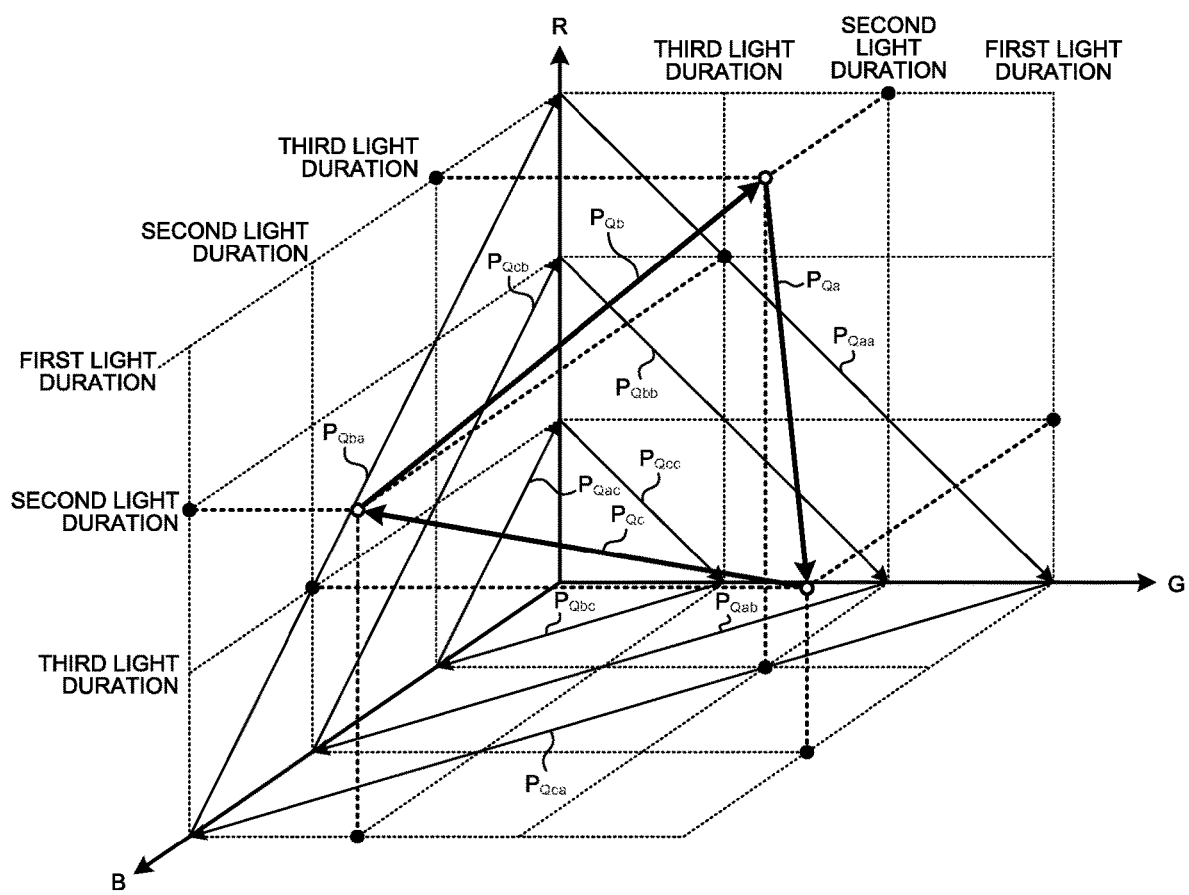
FIG. 18 is a diagram explaining uniqueness of a solution of image signals obtained in the third embodiment.

FIG. 18 is a diagram explaining uniqueness of a solution of image signals obtained in the third embodiment, and illustrating a case where the row vectors Qaa, Qba, and Qca of the matrix $A_{4-11}$, the row vectors Qab, Qbb, and Qcb of the matrix $A_{4-12}$, and the row vectors Qac, Qbc, and Qcc of the matrix $A_{4-13}$ are viewed in an RGB space. FIG. 18 illustrates a case where illumination periods of R, G, and B as first light are the same periods, respective illumination periods of R, G, and B as second light are the same periods, and illumination periods of R, G, and B as third light are the same periods, as well as the illumination period of the first light is three times as long as that of the third light, and the illumination period of the second light is twice as long as that of the third light.

The row vectors Qaa, Qba, and Qca corresponding to the exposure periods of the first light respectively depict loci $P_{Qaa}$, $P_{Qba}$, and $P_{Qca}$ including, as an origin point or an end point, any of three points corresponding to illumination durations of the first light on an R axis, a G axis, and a B axis, on respective planes of an R-G plane, a B-R plane, and a G-B plane. The row vectors Qab, Qbb, and Qcb corresponding to the exposure periods of the second light respectively depict loci $P_{Qab}$, $P_{Qbb}$, and $P_{Qcb}$ including, as an origin point or an end point, any of three points corresponding to illumination durations of the second light on the R axis, the G axis, and the B axis, on respective planes of the R-G plane, the B-R plane, and the G-B plane. The row vectors Qac, Qbc, and Qcc corresponding to the exposure periods of the third light respectively depict loci $P_{Qac}$, $P_{Qbc}$, and $P_{Qcc}$ including, as an origin point or an end point, any of three points corresponding to illumination durations of the third light on the R axis, the G axis, and the B axis, on respective planes of the R-G plane, the B-R plane, and the G-B plane.

As a result, the row vector Qa of the matrix $A_4$, which is a resultant vector of the row vectors Qaa, Qab, and Qac, depicts a locus $P_{Qa}$; the row vector Qb of the matrix $A_4$, which is a resultant vector of the row vectors Qba, Qbb, and Qbc, depicts a locus $P_{Qb}$; the row vector Qc of the matrix $A_4$, which is a resultant vector of the row vectors Qca, Qcb, and Qcc, depicts a locus $P_{Qc}$; and a triangle formed by loci corresponding to the row vectors Qa to Qc has an area. In that case, corresponding loci do not overlap for any of the row vectors Qa to Qc. The row vectors Qa to Qc remain independent and the rank of the matrix $A_4$ is 3. Therefore, there exists an inverse matrix $A_4^{-1}$ of the matrix $A_4$ in Expression (8), and the solution of Expression (8) is unique.

Figure 19:
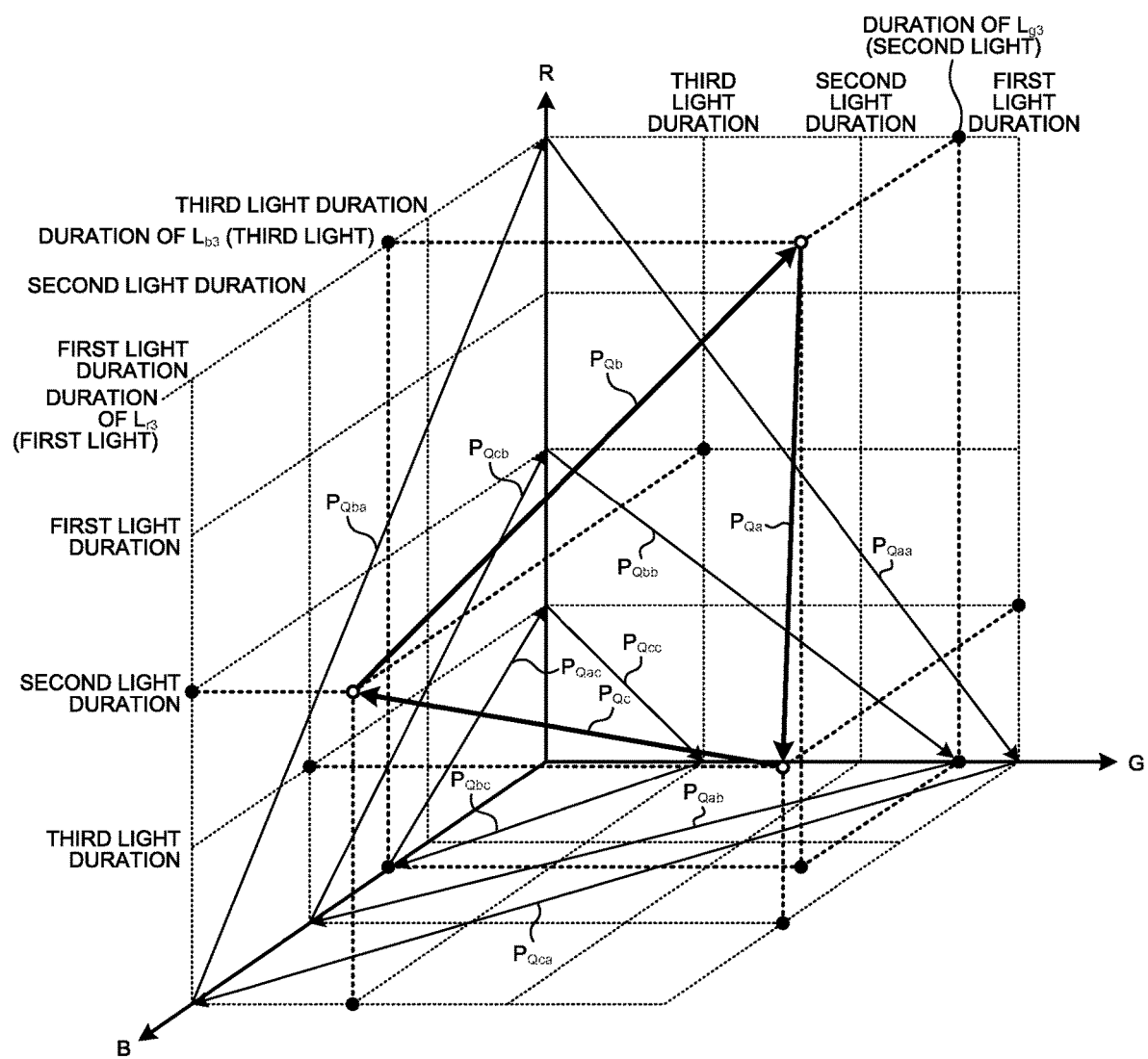
FIG. 19 is a diagram explaining uniqueness of a solution of image signals obtained in the third embodiment.

FIG. 19 is a diagram explaining uniqueness of a solution of image signals obtained in the third embodiment, and illustrating another example of the case where the row vectors Qaa, Qba, and Qca of the matrix $A_{4-11}$, the row vectors Qab, Qbb, and Qcb of the matrix $A_{4-12}$, and the row vectors Qac, Qbc, and Qcc of the matrix $A_{4-13}$ are viewed in the RGB space. A case will be described in which among illumination periods of respective colors, the illumination period $L_{r3}$ of the R light as the first light in frame 3 is prolonged to be (4/3) times as long as the illumination periods of the first light in other frames 1 and 2, the illumination period $L_{g3}$ of the G light as the second light is prolonged to be (4/3) times as long as the illumination periods of the second light in other frames 1 and 2, and the illumination period $L_{b3}$ of the B light as the third light is prolonged to be (4/3) times as long as the illumination periods of the third light in other frames 1 and 2.

In that case, differences from the case illustrated in FIG. 18 reside in that: an origin point of the locus $P_{Qba}$ and an end point of the locus $P_{Qca}$ are at a point corresponding to the illumination period $L_{r3}$ of the R light as the first light in frame 3, which is (4/3) times as long as the illumination periods of the first light in other frames 1 and 2; an origin point of the locus $P_{Qab}$ and an end point of the locus $P_{Qbb}$ are at a point corresponding to the illumination period $L_{g3}$ of the G light as the second light in frame 3, which is (4/3) times as long as the illumination periods of the second light in other frames 1 and 2; and an origin point of the locus $P_{Qac}$ and an end point of the locus $P_{Qbc}$ are at a point corresponding to the illumination period $L_{b3}$ of the B light as the third light in frame 3, which is (4/3) times as long as the illumination periods of the third light in other frames 1 and 2. Also in that case, a triangle formed by the loci $P_{Qa}$, $P_{Qb}$, and $P_{Qc}$ corresponding to the row vectors Qa to Qc has an area, the row vector Qa to Qc remain independent, and the rank of the matrix $A_4$ is 3. Consequently, in the third embodiment, it is possible to change the illumination periods of the first light, the second light, and the third light to periods different from the illumination periods of the first light, the second light, and the third light in other frames.

However, in a case where the illumination periods of the first light, the second light, and the third light in the same frame are all the same periods, the row vectors Qaa, Qbb, and Qcc overlap, the row vectors Qac, Qba, and Qcb overlap, and the row vectors Qab, Qbc, and Qca overlap. In that case, the row vectors Qa to Qc are located at a centroid of a triangle formed by the loci of the row vectors Qaa, Qbb, and Qcc, the row vectors Qac, Qba, and Qcb, and the row vectors Qab, Qbc, and Qca, and fixed. Therefore, the row vectors Qa to Qc are not linearly independent, a rank is not 3, and the solution of Expression (8) is not unique. Consequently, since a condition to maintain the rank of the matrix $A_4$ to be 3 is that a triangle formed by the loci $P_{Qa}$, $P_{Qb}$, and $P_{Qc}$ corresponding to the row vectors Qa to Qc has an area, it is necessary for the illumination controller 334a to perform control such that illumination is performed for illumination periods which are different periods for each of the three colors in the same one-line exposure period. When there is a large difference among the illumination periods of the first light, the second light, and the third light, the area of the triangle formed by the loci $P_{Qa}$, $P_{Qb}$, and $P_{Qc}$ corresponding to the row vectors Qa to Qc increases, which makes it easier to maintain independence of the row vectors Qa to Qc. Accordingly, it is desirable for the illumination controller 334a to set a condition which provides a large difference among the illumination periods of the first light, the second light, and the third light in the same one-line exposure period.

A similar effect to that of the first embodiment is obtained even in a case where light emission is performed with three colors of light in one frame, as in the third embodiment, since an image signal of each color component of a frame to be acquired is extracted in a calculation process using output values of image signals of a plurality of successive frames. Furthermore, in the third embodiment, since illumination frequency of each color further increases as compared to the second embodiment, it is possible to correspondingly reduce the effect of an afterimage occurring when an object moves.

Figure 20:
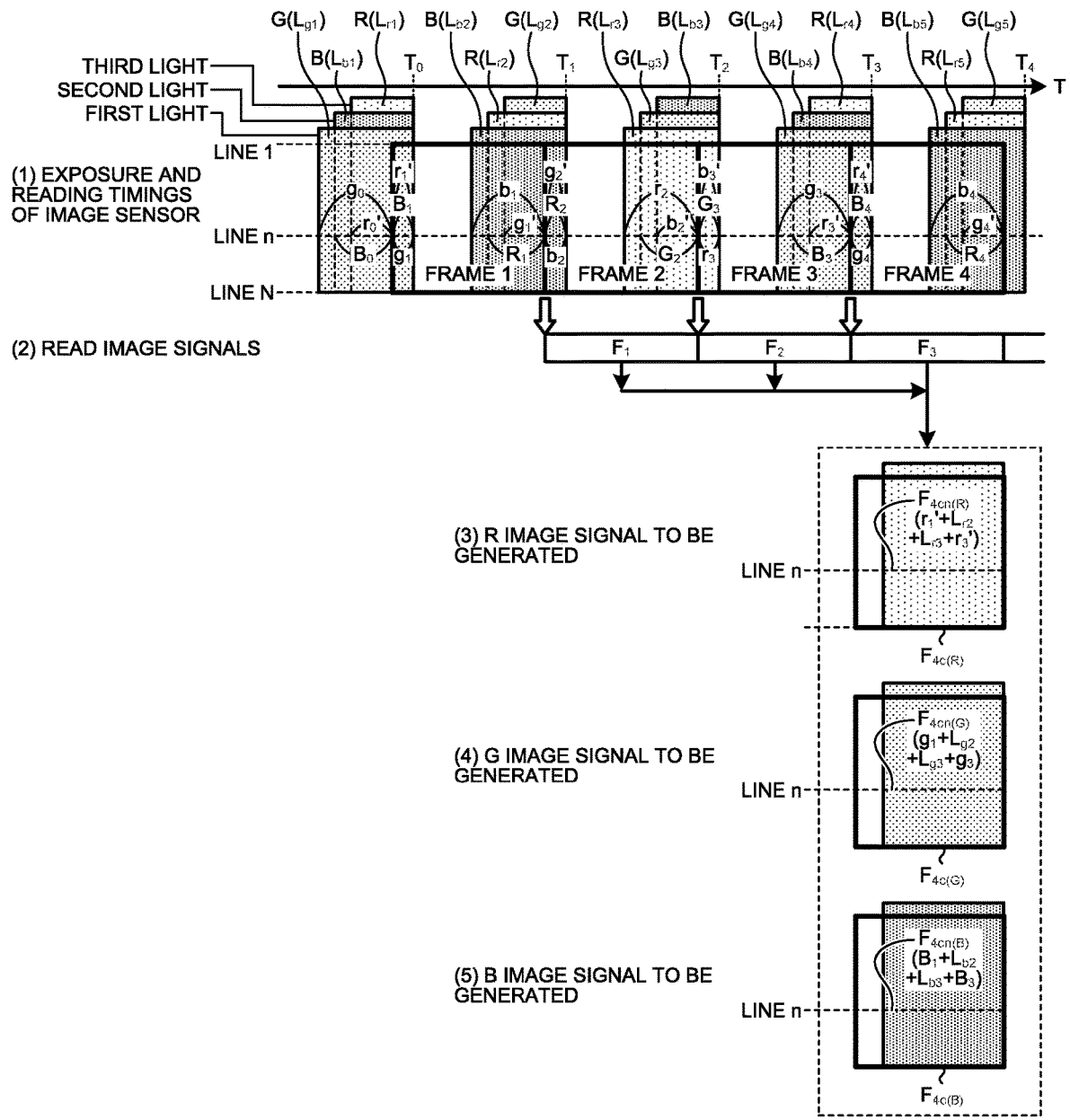
FIG. 20 is a timing chart illustrating exposure and reading timings in a case where the image sensor in the third embodiment is a CCD image sensor.

Similarly to the first and second embodiments, the third embodiment can be applied also to a case where the image sensor 25 is a CCD image sensor which adopts the global shutter method. FIG. 20 is a timing chart illustrating exposure and reading timings in a case where the image sensor 25 is a CCD image sensor. In a case where the illumination controller 334a causes the light source device 4 to perform irradiation with the G light, the B light, and the R light on a condition illustrated in (1) of FIG. 20 to generate, for example, an R image signal $F_{4c(R)}$, a G image signal $F_{4c(G)}$, and a B image signal $F_{4c(B)}$ of the fourth frame, output values of the three successive frame image signals $F_1$ to $F_3$ (see (2) of FIG. 20), which are output values of the same line as the horizontal line to be calculated, are input to Expression (8) to perform calculation for each horizontal line. Also in that case, as with the case of a CMOS image sensor, parameters of a matrix $A_4$ of Expression (8) are respective illumination periods $L_{g1}$, $L_{b2}$, and $L_{r3}$ of the G light, the B light, and the R light as first light, respective illumination periods $L_{b1}$, $L_{r2}$, and $L_{g3}$ of the B light, the R light, and the G light as second light, and respective illumination periods $L_{r1}$, $L_{g2}$, and $L_{b3}$ of the R light, the G light, and the B light as third light in successive frames 1 to 3 regarding the horizontal line n, as well as exposure periods $g_1$ and $g_3$ of the G light as the first light, exposure periods $b_1$ and $b_2$ of the B light as the first light, and exposure periods $r_2$ and $r_3$ of the R light as the first light; exposure periods $B_1$ and $B_3$ of the B light as the second light, exposure periods $R_1$ and $R_2$ of the R light as the second light, and exposure periods $G_2$ and $G_3$ of the G light as the second light; and exposure periods $r_1'$ and $r_3'$ of the R light as the third light, exposure periods $g_1'$ and $g_2'$ of the G light as the third light, and exposure periods $b_2'$ and $b_3'$ of the B light as the third light, to the horizontal line n in frames 1 to 3.

Similarly to the first and second embodiments, the third embodiment can be applied also to the NBI observation method. In that case, the illumination controller 334a may cause an illumination process to be executed such that illumination is performed for illumination periods which are different periods for each of the three colors in the same one-line exposure period. In the illumination process, illumination is performed with illumination light of all three colors in one one-line exposure period on a similar condition to that of irradiation with the R light, the G light, and the B light by using any of patterns of a combination of the V light, the G light, and no light, a combination of the V light, the G light, and VV light, or a combination of the V light, the G light, and GG light. In the third embodiment, the description has been given using, as an example, the case in which illumination with illumination light of three colors is performed such that a period is included during which illumination with the illumination light of all three colors, with which illumination is performed in the same one-line exposure period, is used for illumination in an overlapping manner. However, when the condition is satisfied with which a rank of the matrix $A_4$ of Expression (8) is 3, there is no need for the illumination periods of the illumination light of three colors with which illumination is performed in the same one-line exposure period to overlap.

In the embodiments, the description has been given using, as an example, the processing devices 3, 203, and 303, which are separate devices from the light source device. However, as a matter of course, the embodiments can be applied also to a light source-integrated processing device integrally including a light source. In the embodiments, combinations of illumination light are not limited to a combination of R light, G light, and B light, or a combination of V light with a narrowed bandwidth and the G light. A combination of the G light, excitation light, and excitation light, and a combination of the G light, first R light, and second R light with a wavelength band different from that of the first R light may be employed. As described for the combination example of the V light with a narrowed bandwidth and G light, the embodiments can be applied when wavelength bands of illumination light are different in two times of illumination light emission, which is performed on a three-times basis.

An execution program for each process executed by the processing devices 3, 203, and 303 according to the embodiments, and other constitution unit may be configured so as to be recorded, in an installable or executable file format, in a computer-readable recording medium such as a CD-ROM, a flexible disk, a CD-R, or a digital versatile disk (DVD), and then provided, or may be configured so as to be stored in a computer connected to a network such as the Internet, and then provided through download thereof via the network. Alternatively, the program may be provided or distributed via a network such as the Internet.

According to some embodiments, since an image signal of each color component of a frame to be acquired is obtained for each line through a calculation process using output values of image signals output from an image sensor in a plurality of successive frames in accordance with the number of colors of illumination light, it is possible to expose all pixels for a sufficient period without providing a V-blank period, and to secure a sufficient exposure period for all pixels while suppressing a cable transmission load.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   a light source device configured to sequentially emit illumination light of three colors to irradiate an object in accordance with a predetermined cycle in respective illumination periods;
   an image sensor comprising a plurality of pixels arranged in a matrix, the plurality of pixels being configured to perform photoelectric conversion on light from the object irradiated with the illumination light to generate and output image signals; and
   a processor comprising hardware, wherein the processor is configured to:
   cause the light source device to emit the illumination light of two colors of the three colors such that illumination light of each color of the three colors is emitted a same number of times within three successive one-line exposure periods of the image sensor and the illumination periods of the illumination light of the two colors are at least partially overlapped during a same one-line exposure period of each of the three successive one-line exposure periods of the image sensor; and
   calculate each color component signal for each horizontal line, based on a relational expression using an output value of a horizontal line that is identical to a horizontal line to be calculated, among output values of the image signals in a latest frame, a frame located one frame before the latest frame, and a frame located two frames before the latest frame, using each of the illumination periods per one-line exposure period of each color in each frame, and using each exposure period of each color with respect to the horizontal line to be calculated in each frame to be used for calculation.

2. The endoscope system according to claim 1, wherein the processor is configured to:
   detect brightness of an image from the image signals output from the image sensor;
   obtain the illumination periods of the illumination light of three colors to be emitted by the light source device, based on the brightness of the image detected;
   access a storage configured to store illumination period information indicating a plurality of combinations of illumination periods of the illumination light of three colors to define a unique solution of the relational expression; and
   cause the light source device to emit the illumination light of three colors in a combination of illumination periods closest to the illumination periods of the illumination light of three colors obtained, among the plurality of combinations of illumination periods of the illumination light of three colors indicated in the illumination period information stored in the storage.

3. The endoscope system according to claim 1, wherein the illumination light of three colors is light of red, green, and blue colors.

4. The endoscope system according to claim 1, wherein the image sensor is a complementary metal-oxide semiconductor (CMOS) image sensor.

5. The endoscope system according to claim 4, wherein the processor is configured to cause the light source device to turn off the illumination light concurrently with termination of an exposure period for a first line of the plurality of pixels in the image sensor.

6. The endoscope system according to claim 1, wherein the image sensor is a charge-coupled device (CCD) image sensor.

* * * * *